United States Patent [19]

Suzuki et al.

[11] Patent Number: 5,719,125
[45] Date of Patent: Feb. 17, 1998

[54] HUMAN CHONDROMODULIN-I PROTEIN

[75] Inventors: Fujio Suzuki, Toyonaka; Yuji Hiraki, Takatsuki; Kazuhiro Takahashi, Machida; Junko Suzuki, Hino; Jun Kondo, Machida; Atsuko Kohara, Machida; Akiko Mori, Yokohama; Ei Yamada, Kawasaki, all of Japan

[73] Assignee: Mitsubishi Chemical Corporation, Tokyo, Japan

[21] Appl. No.: 241,465

[22] Filed: May 11, 1994

[30] Foreign Application Priority Data

May 11, 1993 [JP] Japan ................. 5-109620
Dec. 17, 1993 [JP] Japan ................. 5-318298

[51] Int. Cl.$^6$ ........................................... A61K 38/17
[52] U.S. Cl. ................ 514/12; 530/350; 530/399; 435/69.1; 435/320.1; 435/252.3; 435/325
[58] Field of Search .................... 530/350, 399; 514/12; 435/69.1, 320.1, 252.3, 240, 325

[56] References Cited

U.S. PATENT DOCUMENTS 5,444,157  8/1995  Suzuki et al. ..................... 530/395

FOREIGN PATENT DOCUMENTS 0473080  3/1992  European Pat. Off. .

OTHER PUBLICATIONS

Takigawa et al. Anticancer Res. (1990) 10, 311–316.
Hiraki et al. Biochem. Biophys. Res. Comm. (1991) 175, 971–977.
*Chemical Abstracts*, vol. 115, No. 15, Oct. 14, 1991, Y. Hiraki et al., "Molecular Cloning of a New Class of Cartilage–Specific Matrix, Chondromodulin–I, Which Stimulates Growth of Cultured Chondrocytes", p. 270.

*Primary Examiner*—John Ulm
*Assistant Examiner*—Karen E. Brown
*Attorney, Agent, or Firm*—Wenderoth, Lind & Ponack

[57] ABSTRACT

A novel human chondromodulin-I protein having a molecular weight of about 26,000 dalton on SDS-PAGE and capable of stimulating the growth of chondrocytes with or without FGF, promoting the differential potency of these cells, and inhibiting the growth of vascular endothelial cells, a DNA encoding this protein, expression vector containing the DNA, a transformant capable of producing recombinant chondromodulin-I protein, a process for producing chondromodulin-I protein by culturing the transformant and a pharmaceutical composition containing chondromodulin-I protein as an active ingredient.

8 Claims, No Drawings

SEQUENCE LISTING ( 1 ) GENERAL INFORMATION:

( i i i ) NUMBER OF SEQUENCES:21

( 2 ) INFORMATION FOR SEQ ID NO:1:

( i ) SEQUENCE CHARACTERISTICS:
        ( A ) LENGTH: 1000 base pairs
        ( B ) TYPE: nucleic acid
        ( C ) STRANDEDNESS: double
        ( D ) TOPOLOGY: linear ( v i ) ORIGINAL SOURCE:
        ( A ) ORGANISM: Human being (Homo Sapiens)

( v i i ) IMMEDIATE SOURCE:
        ( B ) CLONE: 411; SUBCLONE: p411BS ( i x ) FEATURE:
        ( A ) NAME/KEY: exon
        ( B ) LOCATION: 161 ... 232

( i x ) FEATURE:
        ( A ) NAME/KEY: exon
        ( B ) LOCATION: 691 ... 834
        ( C ) IDENTIFICATION METHOD: E ( x i ) SEQUENCE DESCRIPTION: SEQ ID NO:1:

```
AGGTGAGGCG  CTAGAAGGGG  TGGGGACCGC  TGGGCTGGCC  CAGGCGGGAC  CGTGCACCGT         60

GTGTGCGCGC  GGCGTTGAAA  TGCCCTGCAC  GTCGGGGCAG  CGGGACAGAT  CCCAGGGTGC        120

CCAGGGAGTC  TCCAAGTGCC  TCACTCCTCC  CGCCGCAAAC  ATG ACA GAG AAC TCC           175
                                                Met Thr Glu Asn Ser
                                                  1               5

GAC AAA GTT CCC ATT GCC CTG GTG GGA CCT GAT GAC GTG GAA TTC TGC              223
Asp Lys Val Pro Ile Ala Leu Val Gly Pro Asp Asp Val Glu Phe Cys
             10                  15                  20

AGC CCC CCG GTGAGTAC CGCCAGGGAT CCACACGCA GGGCCTGGGT TGTGTGAGTA              280
Ser Pro Pro
         24

TCAGGTTCCA  CAGTTCGGAC  TCAGGGGTGC  GTGCCACCGA  ATGGGTGTGT  TGGCGGGGGA        340

ATAAATTTGG  GTCCCAAATG  TGTGGGTGGG  ATGTCGCCCC  ACGCGTATGA  GTGTGCAGGG        400

GTCACGGCAT  CCACAGGCGG  GTGCGGAGGG  ACGTCCCGTG  GCCGGTAGAG  GGTGCAGGTC        460

CTGGGGCGAA  GGCCCTGTGC  TGCGGGGTTT  GCTCATCCCA  CTTCCACGCC  CGACTGCAAA        520

GGACCCTCGG  GAGGGAGCGC  GGCGAAAGGG  CACCCGTAG  GAGCCCGGGC  GAGCTGTTTC         580

CCGCCCGACT  CCCCACTCCC  TGGGGGCTAC  CGCGTGGGGC  CCGGGTGCGC  TGGGGGCCGC        640

AGGTGCTGGC  GGCACAAACG  CGACGGTCCC  TCTCCCGCCC  CGGCCCGCAG  GCG TAC           696
                                                            Ala Tyr
                                                             25

GCT ACG CTG ACG GTG AAG CCC TCC AGC CCC GCG CGG CTG CTC AAG GTG              744
Ala Thr Leu Thr Val Lys Pro Ser Ser Pro Ala Arg Leu Leu Lys Val
             30                  35                  40

GGA GCC GTG GTC CTC ATT TCG GGA GCT GTG CTG CTC TTT GGG GCC                  792
Gly Ala Val Val Leu Ile Ser Gly Ala Val Leu Leu Leu Phe Gly Ala
             45                  50                  55

ATC GGG GCC TTC TAC TTC TGG AAG GGG AGC GAC AGT CAC ATT AGTCCA               840
```

```
Ile Gly Ala Phe Tyr Phe Trp Lys Gly Ser Asp Ser His Ile
     60                  65                  70
```

| | | | | |
|---|---|---|---|---|
| GAGGGCGGCG | CGCGGGGACC | CCCGTGTCGC | CCATGGTGCC | CCTAGGGGGG GCCCGAGCGC | 900 |
| GGGCCGGCGA | GGGGCGCGCG | GCTGCCCGGC | GGCCCCTCGG | GCCCAGCGTG AGCTCCCTC | 960 |
| TCCCATCCCA | CTCTGGCACG | CGGCTTTCCG | CCTTAGGTCA | | 1000 |

( 2 ) INFORMATION FOR SEQ ID NO:2:

( i ) SEQUENCE CHARACTERISTICS:
        ( A ) LENGTH: 1006 base pairs
        ( B ) TYPE: nucleic acid
        ( C ) STRANDEDNESS: double
        ( D ) TOPOLOGY: linear ( v i ) ORIGINAL SOURCE:
        ( A ) ORGANISM: Human being (Homo Sapiens)

( v i i ) IMMEDIATE SOURCE:
        ( B ) CLONE: phCHM-I3-6

( i x ) FEATURE:
        ( A ) NAME/KEY: P CDS
        ( B ) LOCATION: 2 .. 1003
        ( C ) IDENTIFICATION METHOD: E ( x i ) SEQUENCE DESCRIPTION: SEQ ID NO:2:

```
C ATG ACA GAG AAC TCC GAC AAA GTT CCC ATT GCC CTG GTG GGA CCT GAT    49
  Met Thr Glu Asn Ser Asp Lys Val Pro Ile Ala Leu Val Gly Pro Asp
  1               5                  10                  15

GAC GTG GAA TTC TGC AGC CCC CCG GCG TAC GCT ACG CTG ACG GTG AAG       97
Asp Val Glu Phe Cys Ser Pro Pro Ala Tyr Ala Thr Leu Thr Val Lys
                20                  25                  30

CCC TCC AGC CCC GCG CGG CTG CTC AAG GTG GGA GCC GTG GTC CTC ATT      145
Pro Ser Ser Pro Ala Arg Leu Leu Lys Val Gly Ala Val Val Leu Ile
            35                  40                  45

TCG GGA GCT GTG CTG CTG CTC TTT GGG GCC ATC GGG GCC TTC TAC TTC      193
Ser Gly Ala Val Leu Leu Leu Phe Gly Ala Ile Gly Ala Phe Tyr Phe
        50                  55                  60

TGG AAG GGG AGC GAC AGT CAC ATT TAC AAT GTC CAT TAC ACC ATG AGT      241
Trp Lys Gly Ser Asp Ser His Ile Tyr Asn Val His Tyr Thr Met Ser
65                  70                  75                  80

ATC AAT GGG AAA CTA CAA GAT GGG TCA ATG GAA ATA GAC GCT GGG AAC      289
Ile Asn Gly Lys Leu Gln Asp Gly Ser Met Glu Ile Asp Ala Gly Asn
                85                  90                  95

AAC TTG GAG ACC TTT AAA ATG GGA AGT GGA GCT GAA GAA GCA ATT GCA      337
Asn Leu Glu Thr Phe Lys Met Gly Ser Gly Ala Glu Glu Ala Ile Ala
            100                 105                 110

GTT AAT GAT TTC CAG AAT GGC ATC ACA GGA ATT CGT TTT GCT GGA GGA      385
Val Asn Asp Phe Gln Asn Gly Ile Thr Gly Ile Arg Phe Ala Gly Gly
        115                 120                 125

GAG AAG TGC TAC ATT AAA GCG CAA GTG AAG GCT CGT ATT CCT GAG GTG      433
Glu Lys Cys Tyr Ile Lys Ala Gln Val Lys Ala Arg Ile Pro Glu Val
130                 135                 140

GGC GCC GTG ACC AAA CAG AGC ATC TCC TCC AAA CTG GAA GGC AAG ATC      481
Gly Ala Val Thr Lys Gln Ser Ile Ser Ser Lys Leu Glu Gly Lys Ile
145                 150                 155                 160

ATG CCA GTC AAA TAT GAA GAA AAT TCT CTT ATC TGG GTG GCT GTA GAT      529
Met Pro Val Lys Tyr Glu Glu Asn Ser Leu Ile Trp Val Ala Val Asp
                165                 170                 175

CAG CCT GTG AAG GAC AAC AGC TTC TTG AGT TCT AAG GTG TTA GAA CTC      577
Gln Pro Val Lys Asp Asn Ser Phe Leu Ser Ser Lys Val Leu Glu Leu
            180                 185                 190
```

```
TGC  GGT  GAC  CTT  CCT  ATT  TTC  TGG  CTT  AAA  CCA  ACC  TAT  CCA  AAA  GAA     625
Cys  Gly  Asp  Leu  Pro  Ile  Phe  Trp  Leu  Lys  Pro  Thr  Tyr  Pro  Lys  Glu
          195                      200                     205

ATC  CAG  AGG  GAA  AGA  AGA  GAA  GTG  GTA  AGA  AAA  ATT  GTT  CCA  ACT  ACC     673
Ile  Gln  Arg  Glu  Arg  Arg  Glu  Val  Val  Arg  Lys  Ile  Val  Pro  Thr  Thr
          210                      215                     220

ACA  AAA  AGA  CCA  CAC  AGT  GGA  CCA  CGG  AGC  AAC  CCA  GGC  GCT  GGA  AGA     721
Thr  Lys  Arg  Pro  His  Ser  Gly  Pro  Arg  Ser  Asn  Pro  Gly  Ala  Gly  Arg
225                           230                     235                     240

CTG  AAT  AAT  GAA  ACC  AGA  CCC  AGT  GTT  CAA  GAG  GAC  TCA  CAA  GCC  TTC     769
Leu  Asn  Asn  Glu  Thr  Arg  Pro  Ser  Val  Gln  Glu  Asp  Ser  Gln  Ala  Phe
                    245                      250                     255

AAT  CCT  GAT  AAT  CCT  TAT  CAT  CAG  CAG  GAA  GGG  GAA  AGC  ATG  ACA  TTC     817
Asn  Pro  Asp  Asn  Pro  Tyr  His  Gln  Gln  Glu  Gly  Glu  Ser  Met  Thr  Phe
               260                      265                     270

GAC  CCT  AGA  CTG  GAT  CAC  GAA  GGA  ATC  TGT  TGT  ATA  GAA  TGT  AGG  CGG     865
Asp  Pro  Arg  Leu  Asp  His  Glu  Gly  Ile  Cys  Cys  Ile  Glu  Cys  Arg  Arg
          275                      280                     285

AGC  TAC  ACC  CAC  TGC  CAG  AAG  ATC  TGT  GAA  CCC  CTG  GGG  GGC  TAT  TAC     913
Ser  Tyr  Thr  His  Cys  Gln  Lys  Ile  Cys  Glu  Pro  Leu  Gly  Gly  Tyr  Tyr
          290                      295                     300

CCA  TGG  CCT  TAT  AAT  TAT  CAA  GGC  TGC  CGT  TCG  GCC  TGC  AGA  GTC  ATC     961
Pro  Trp  Pro  Tyr  Asn  Tyr  Gln  Gly  Cys  Arg  Ser  Ala  Cys  Arg  Val  Ile
305                           310                     315                     320

ATG  CCA  TGT  AGC  TGG  TGG  GTG  GCC  CGC  ATC  CTG  GGC  ATG  GTG  TAA          1006
Met  Pro  Cys  Ser  Trp  Trp  Val  Ala  Arg  Ile  Leu  Gly  Met  Val  Stop
                    325                      330                     335
```

( 2 ) INFORMATION FOR SEQ ID NO:3:

( i ) SEQUENCE CHARACTERISTICS:
        ( A ) LENGTH: 1006 base pairs
        ( B ) TYPE: nucleic acid
        ( C ) STRANDEDNESS: double
        ( D ) TOPOLOGY: linear ( v i ) ORIGINAL SOURCE:
        ( A ) ORGANISM: Human being (Homo Sapiens)

( v i i i ) IMMEDIATE SOURCE:
        ( B ) CLONE: phCHM-I6-3

( i x ) FEATURE:
        ( A ) NAME/KEY: P CDS
        ( B ) LOCATION: 2 .. 1003
        ( C ) IDENTIFICATION METHOD: E ( x i ) SEQUENCE DESCRIPTION: SEQ ID NO:3:

```
C  ATG  ACA  GAG  AAC  TCC  GAC  AAA  GTT  CCC  ATT  GCC  CTG  GTG  GGA  CCT  GAT      49
   Met  Thr  Glu  Asn  Ser  Asp  Lys  Val  Pro  Ile  Ala  Leu  Val  Gly  Pro  Asp
   1                   5                      10                      15

GAC  GTG  GAA  TTC  TGC  AGC  CCC  CCG  GCG  TAC  GCT  ACG  CTG  ACG  GTG  AAG         97
Asp  Val  Glu  Phe  Cys  Ser  Pro  Pro  Ala  Tyr  Ala  Thr  Leu  Thr  Val  Lys
               20                      25                      30

CCC  TCC  AGC  CCC  GCG  CGG  CTG  CTC  AAG  GTG  GGA  GCC  GTG  GTC  CTC  ATT        145
Pro  Ser  Ser  Pro  Ala  Arg  Leu  Leu  Lys  Val  Gly  Ala  Val  Val  Leu  Ile
          35                      40                      45

TCG  GGA  GCT  GTG  CTG  CTG  CTC  TTT  GGG  GCC  ATC  GGG  GCC  TTC  TAC  TTC        193
Ser  Gly  Ala  Val  Leu  Leu  Leu  Phe  Gly  Ala  Ile  Gly  Ala  Phe  Tyr  Phe
          50                      55                      60

TGG  AAG  GGG  AGC  GAC  AGT  CAC  ATT  TAC  AAT  GTC  CAT  TAC  ACC  ATG  AGT        241
Trp  Lys  Gly  Ser  Asp  Ser  His  Ile  Tyr  Asn  Val  His  Tyr  Thr  Met  Ser
65                       70                      75                           80

ATC  AAT  GGG  AAA  CTA  CAA  GAT  GGG  TCA  ATG  GAA  ATA  GAC  GCT  GGG  AAC        289
Ile  Asn  Gly  Lys  Leu  Gln  Asp  Gly  Ser  Met  Glu  Ile  Asp  Ala  Gly  Asn
```

|  |  |  |  |  |  |  |  |  |  |  |  |  |  |  |  |
|---|---|---|---|---|---|---|---|---|---|---|---|---|---|---|---|
|  |  |  |  | 85 |  |  |  | 90 |  |  |  | 95 |  |  |  |
| AAC | TTG | GAG | ACC | TTT | AAA | ATG | GGA | AGT | GGA | GCT | GAA | GAA | GCA | ATT | GCA | 337 |
| Asn | Leu | Glu | Thr | Phe | Lys | Met | Gly | Ser | Gly | Ala | Glu | Glu | Ala | Ile | Ala |
|  |  |  | 100 |  |  |  |  | 105 |  |  |  | 110 |  |  |  |
| GTT | AAT | GAT | TTC | CAG | AAT | GGC | ATC | ACA | GGA | ATT | CGT | TTT | GCT | GGA | GGA | 385 |
| Val | Asn | Asp | Phe | Gln | Asn | Gly | Ile | Thr | Gly | Ile | Arg | Phe | Ala | Gly | Gly |
|  |  | 115 |  |  |  | 120 |  |  |  |  | 125 |  |  |  |  |
| GAG | AAG | TGC | TAC | ATT | AAA | GCG | CAA | GTG | AAG | GCT | CGT | ATT | CCT | GAG | GTG | 433 |
| Glu | Lys | Cys | Tyr | Ile | Lys | Ala | Gln | Val | Lys | Ala | Arg | Ile | Pro | Glu | Val |
|  | 130 |  |  |  |  | 135 |  |  |  |  | 140 |  |  |  |  |
| GGC | GCC | GTG | ACC | AAA | CAG | AGC | ATC | TCC | TCC | AAA | CTG | GAA | GGC | AAG | ATC | 481 |
| Gly | Ala | Val | Thr | Lys | Gln | Ser | Ile | Ser | Ser | Lys | Leu | Glu | Gly | Lys | Ile |
| 145 |  |  |  |  | 150 |  |  |  |  | 155 |  |  |  |  | 160 |
| ATG | CCA | GTC | AAA | TAT | GAA | GAA | AAT | TCT | CTT | ATC | TGG | GTG | GCT | GTA | GAT | 529 |
| Met | Pro | Val | Lys | Tyr | Glu | Glu | Asn | Ser | Leu | Ile | Trp | Val | Ala | Val | Asp |
|  |  |  |  | 165 |  |  |  |  | 170 |  |  |  |  | 175 |  |
| CAG | CCT | GTG | AAG | GAC | AAC | AGC | TTC | TTG | AAT | TCT | AAG | GTG | TTA | GAA | CTC | 577 |
| Gln | Pro | Val | Lys | Asp | Asn | Ser | Phe | Leu | Asn | Ser | Lys | Val | Leu | Glu | Leu |
|  |  |  | 180 |  |  |  |  | 185 |  |  |  | 190 |  |  |  |
| TGC | GGT | GAC | CTT | CCT | ATT | TTC | TGG | CTT | AAA | CCA | ACC | TAT | CCA | AAA | GAA | 625 |
| Cys | Gly | Asp | Leu | Pro | Ile | Phe | Trp | Leu | Lys | Pro | Thr | Tyr | Pro | Lys | Glu |
|  |  | 195 |  |  |  |  | 200 |  |  |  | 205 |  |  |  |  |
| ATC | CAG | AGG | GAA | AGA | AGA | GAA | GTG | GTA | AGA | AAA | ATT | GTT | CCA | ACT | ACC | 673 |
| Ile | Gln | Arg | Glu | Arg | Arg | Glu | Val | Val | Arg | Lys | Ile | Val | Pro | Thr | Thr |
|  | 210 |  |  |  |  | 215 |  |  |  |  | 220 |  |  |  |  |
| ACA | AAA | AGA | CCA | CAC | AGT | GGA | CCA | CGG | AGC | AAC | CCA | GGC | GCT | GGA | AGA | 721 |
| Thr | Lys | Arg | Pro | His | Ser | Gly | Pro | Arg | Ser | Asn | Pro | Gly | Ala | Gly | Arg |
| 225 |  |  |  |  | 230 |  |  |  |  | 235 |  |  |  |  | 240 |
| CTG | AAT | AAT | GAA | ACC | AGA | CCC | AGT | GTT | CAA | GAG | GAC | TCA | CAA | GCC | TTC | 769 |
| Leu | Asn | Asn | Glu | Thr | Arg | Pro | Ser | Val | Gln | Glu | Asp | Ser | Gln | Ala | Phe |
|  |  |  |  | 245 |  |  |  |  | 250 |  |  |  |  | 255 |  |
| AAT | CCT | GAT | AAT | CCT | TAT | CAT | CAG | CAG | GAA | GGG | GAA | AGC | ATG | ACA | TTC | 817 |
| Asn | Pro | Asp | Asn | Pro | Tyr | His | Gln | Gln | Glu | Gly | Glu | Ser | Met | Thr | Phe |
|  |  |  | 260 |  |  |  |  | 265 |  |  |  | 270 |  |  |  |
| GAC | CCT | AGA | CTG | GAT | CAC | GAA | GGA | ATC | TGT | TGT | ATA | GAA | TGT | AGG | CGG | 865 |
| Asp | Pro | Arg | Leu | Asp | His | Glu | Gly | Ile | Cys | Cys | Ile | Glu | Cys | Arg | Arg |
|  |  | 275 |  |  |  |  | 280 |  |  |  | 285 |  |  |  |  |
| AGC | TAC | ACC | CAC | TGC | CAG | AAG | ATC | TGT | GAA | CCC | CTG | GGG | GGC | TAT | TAC | 913 |
| Ser | Tyr | Thr | His | Cys | Gln | Lys | Ile | Cys | Glu | Pro | Leu | Gly | Gly | Tyr | Tyr |
|  | 290 |  |  |  |  | 295 |  |  |  | 300 |  |  |  |  |  |
| CCA | TGG | CCT | TAT | AAT | TAT | CAA | GGC | TGC | CGT | TCG | GCC | TGC | AGA | GTC | ATC | 961 |
| Pro | Trp | Pro | Tyr | Asn | Tyr | Gln | Gly | Cys | Arg | Ser | Ala | Cys | Arg | Val | Ile |
| 305 |  |  |  |  | 310 |  |  |  | 315 |  |  |  |  | 320 |  |
| ATG | CCA | TGT | AGC | TGG | TGG | GTG | GCC | CGC | ATC | CTG | GGC | ATG | GTG | TAA |  | 1006 |
| Met | Pro | Cys | Ser | Trp | Trp | Val | Ala | Arg | Ile | Leu | Gly | Met | Val | Stop |  |
|  |  |  | 325 |  |  |  |  | 330 |  |  |  |  | 335 |  |  |

( 2 ) INFORMATION FOR SEQ ID NO:4:

( i ) SEQUENCE CHARACTERISTICS:
        ( A ) LENGTH: 892 base pairs
        ( B ) TYPE: nucleic acid
        ( C ) STRANDEDNESS: double
        ( D ) TOPOLOGY: linear ( v i ) ORIGINAL SOURCE:
        ( A ) ORGANISM: Human being (Homo Sapiens)

( v i i ) IMMEDIATE SOURCE:
        ( B ) CLONE: phCHM-I6-5

( i x ) FEATURE:
        ( A ) NAME/KEY: P CDS
        ( B ) LOCATION: 2 .. 889

( C ) IDENTIFICATION METHOD: E ( x i ) SEQUENCE DESCRIPTION: SEQ ID NO:4:

```
C ATG ACA GAG AAC TCC GAC AAA GTT CCC ATT GCC CTG GTG GGA CCT GAT        49
  Met Thr Glu Asn Ser Asp Lys Val Pro Ile Ala Leu Val Gly Pro Asp
  1             5                  10                  15

GAC GTG GAA TTC TGC AGC CCC CCG GCG TAC GCT ACG CTG ACG GTG AAG          97
Asp Val Glu Phe Cys Ser Pro Pro Ala Tyr Ala Thr Leu Thr Val Lys
            20                  25                  30

CCC TCC AGC CCC GCG CGG CTG CTC AAG GTG GGA GCC GTG GTC CTC ATT        145
Pro Ser Ser Pro Ala Arg Leu Leu Lys Val Gly Ala Val Val Leu Ile
        35                  40                  45

TCG GGA GCT GTG CTG CTG CTC TTT GGG GCC ATC GGG GCC TTC TAC TTC        193
Ser Gly Ala Val Leu Leu Leu Phe Gly Ala Ile Gly Ala Phe Tyr Phe
    50                  55                  60

TGG AAG GGG AGC GAC AGT CAC ATT TAC AAT GTC CAT TAC ACC ATG AGT        241
Trp Lys Gly Ser Asp Ser His Ile Tyr Asn Val His Tyr Thr Met Ser
65                  70                  75                  80

ATC AAT GGG AAA TTA CAA GAT GGG TCA ATG GAA ATA GAC GCT GGG AAC        289
Ile Asn Gly Lys Leu Gln Asp Gly Ser Met Glu Ile Asp Ala Gly Asn
                85                  90                  95

AAC TTG GAG ACC TTT AAA ATG GGA AGT GGA GCT GAA GAA GCA ATT GCA        337
Asn Leu Glu Thr Phe Lys Met Gly Ser Gly Ala Glu Glu Ala Ile Ala
            100                 105                 110

GTT AAT GAT TTC CAG AAT GAA GGC AAG ATC ATG CCA GTC AAA TAT GAA        385
Val Asn Asp Phe Gln Asn Glu Gly Lys Ile Met Pro Val Lys Tyr Glu
        115                 120                 125

GAA AAT TCT CTT ATC TGG GTG GCT GTA GAT CAG CCT GTG AAG GAC AAC        433
Glu Asn Ser Leu Ile Trp Val Ala Val Asp Gln Pro Val Lys Asp Asn
130                 135                 140

AGC TTC TTG AGT TCT AAG GTG TTA GAA CTC TGC GGT GAC CTT CCT ATT        481
Ser Phe Leu Ser Ser Lys Val Leu Glu Leu Cys Gly Asp Leu Pro Ile
145                 150                 155                 160

TCC TGG CTT AAA CCA ACC TAT CCA AAA GAA ATC CAG AGG GAA AGA AGA        529
Ser Trp Leu Lys Pro Thr Tyr Pro Lys Glu Ile Gln Arg Glu Arg Arg
                165                 170                 175

GAA GTG GTA AGA AAA ATT GTT CCA ACT ACC ACA AAA AGA CCA CAC AAT        577
Glu Val Val Arg Lys Ile Val Pro Thr Thr Thr Lys Arg Pro His Asn
            180                 185                 190

GGA CCA CGG AGC AAC CCA GGC GCT GGA AGA CTG AAT AAT GAA ACC AGA        625
Gly Pro Arg Ser Asn Pro Gly Ala Gly Arg Leu Asn Asn Glu Thr Arg
        195                 200                 205

CCC AGT GTT CAA GAG GAC TCA CAA GCC TTC AAT CCT GAT AAT CCT TAT        673
Pro Ser Val Gln Glu Asp Ser Gln Ala Phe Asn Pro Asp Asn Pro Tyr
    210                 215                 220

CAT CAG CAG GAA GGG GAA AGC ATG ACA TTC GAC CCT AGA CTG GAT CAC        721
His Gln Gln Glu Gly Glu Ser Met Thr Phe Asp Pro Arg Leu Asp His
225                 230                 235                 240

GAA GGA ATC TGT TGT ATA GAA TGT AGG CGG AGC TAC ACC CAC TGC CAG        769
Glu Gly Ile Cys Cys Ile Glu Cys Arg Arg Ser Tyr Thr His Cys Gln
                245                 250                 255

AAG ATC TGT GAA CCC CTG GGG GGC TAT TAC CCA TGG CCT TAT AAT TAT        817
Lys Ile Cys Glu Pro Leu Gly Gly Tyr Tyr Pro Trp Pro Tyr Asn Tyr
            260                 265                 270

CAA GGC TGC CGT TCG GCC TGC AGA GTC ATC ATG CCA TGT AGC TGG TGG        865
Gln Gly Cys Arg Ser Ala Cys Arg Val Ile Met Pro Cys Ser Trp Trp
        275                 280                 285

GTG GCC CGC ATC CTG GGC ATG GTG TAA                                    892
Val Ala Arg Ile Leu Gly Met Val Stop
    290                 295
```

( 2 ) INFORMATION FOR SEQ ID NO:5:

( i ) SEQUENCE CHARACTERISTICS:
        ( A ) LENGTH: 1006 base pairs
        ( B ) TYPE: nucleic acid
        ( C ) STRANDEDNESS: double
        ( D ) TOPOLOGY: linear ( v i ) ORIGINAL SOURCE:
        ( A ) ORGANISM: Human being (Homo Sapiens)

( i x ) FEATURE:
        ( A ) NAME/KEY: P CDS
        ( B ) LOCATION: 2..1003
        ( C ) IDENTIFICATION METHOD: E ( x i ) SEQUENCE DESCRIPTION: SEQ ID NO:5:

```
C  ATG  ACA  GAG  AAC  TCC  GAC  AAA  GTT  CCC  ATT  GCC  CTG  GTG  GGA  CCT  GAT       49
   Met  Thr  Glu  Asn  Ser  Asp  Lys  Val  Pro  Ile  Ala  Leu  Val  Gly  Pro  Asp
   1              5                        10                       15

GAC  GTG  GAA  TTC  TGC  AGC  CCC  CCG  GCG  TAC  GCT  ACG  CTG  ACG  GTG  AAG            97
Asp  Val  Glu  Phe  Cys  Ser  Pro  Pro  Ala  Tyr  Ala  Thr  Leu  Thr  Val  Lys
                    20                       25                       30

CCC  TCC  AGC  CCC  GCG  CGG  CTG  CTC  AAG  GTG  GGA  GCC  GTG  GTC  CTC  ATT           145
Pro  Ser  Ser  Pro  Ala  Arg  Leu  Leu  Lys  Val  Gly  Ala  Val  Val  Leu  Ile
               35                       40                       45

TCG  GGA  GCT  GTG  CTG  CTG  CTC  TTT  GGG  GCC  ATC  GGG  GCC  TTC  TAC  TTC           193
Ser  Gly  Ala  Val  Leu  Leu  Leu  Phe  Gly  Ala  Ile  Gly  Ala  Phe  Tyr  Phe
     50                       55                       60

TGG  AAG  GGG  AGC  GAC  AGT  CAC  ATT  TAC  AAT  GTC  CAT  TAC  ACC  ATG  AGT           241
Trp  Lys  Gly  Ser  Asp  Ser  His  Ile  Tyr  Asn  Val  His  Tyr  Thr  Met  Ser
65                       70                       75                       80

ATC  AAT  GGG  AAA  CTA  CAA  GAT  GGG  TCA  ATG  GAA  ATA  GAC  GCT  GGG  AAC           289
Ile  Asn  Gly  Lys  Leu  Gln  Asp  Gly  Ser  Met  Glu  Ile  Asp  Ala  Gly  Asn
                    85                       90                       95

AAC  TTG  GAG  ACC  TTT  AAA  ATG  GGA  AGT  GGA  GCT  GAA  GAA  GCA  ATT  GCA           337
Asn  Leu  Glu  Thr  Phe  Lys  Met  Gly  Ser  Gly  Ala  Glu  Glu  Ala  Ile  Ala
               100                      105                      110

GTT  AAT  GAT  TTC  CAG  AAT  GGC  ATC  ACA  GGA  ATT  CGT  TTT  GCT  GGA  GGA           385
Val  Asn  Asp  Phe  Gln  Asn  Gly  Ile  Thr  Gly  Ile  Arg  Phe  Ala  Gly  Gly
          115                      120                      125

GAG  AAG  TGC  TAC  ATT  AAA  GCG  CAA  GTG  AAG  GCT  CGT  ATT  CCT  GAG  GTG           433
Glu  Lys  Cys  Tyr  Ile  Lys  Ala  Gln  Val  Lys  Ala  Arg  Ile  Pro  Glu  Val
     130                      135                      140

GGC  GCC  GTG  ACC  AAA  CAG  AGC  ATC  TCC  TCC  AAA  CTG  GAA  GGC  AAG  ATC           481
Gly  Ala  Val  Thr  Lys  Gln  Ser  Ile  Ser  Ser  Lys  Leu  Glu  Gly  Lys  Ile
145                      150                      155                      160

ATG  CCA  GTC  AAA  TAT  GAA  GAA  AAT  TCT  CTT  ATC  TGG  GTG  GCT  GTA  GAT           529
Met  Pro  Val  Lys  Tyr  Glu  Glu  Asn  Ser  Leu  Ile  Trp  Val  Ala  Val  Asp
                    165                      170                      175

CAG  CCT  GTG  AAG  GAC  AAC  AGC  TTC  TTG  AGT  TCT  AAG  GTG  TTA  GAA  CTC           577
Gln  Pro  Val  Lys  Asp  Asn  Ser  Phe  Leu  Ser  Ser  Lys  Val  Leu  Glu  Leu
               180                      185                      190

TGC  GGT  GAC  CTT  CCT  ATT  TTC  TGG  CTT  AAA  CCA  ACC  TAT  CCA  AAA  GAA           625
Cys  Gly  Asp  Leu  Pro  Ile  Phe  Trp  Leu  Lys  Pro  Thr  Tyr  Pro  Lys  Glu
          195                      200                      205

ATC  CAG  AGG  GAA  AGA  AGA  GAA  GTG  GTA  AGA  AAA  ATT  GTT  CCA  ACT  ACC           673
Ile  Gln  Arg  Glu  Arg  Arg  Glu  Val  Val  Arg  Lys  Ile  Val  Pro  Thr  Thr
     210                      215                      220

ACA  AAA  AGA  CCA  CAC  AGT  GGA  CCA  CGG  AGC  AAC  CCA  GGC  GCT  GGA  AGA           721
Thr  Lys  Arg  Pro  His  Ser  Gly  Pro  Arg  Ser  Asn  Pro  Gly  Ala  Gly  Arg
225                      230                      235                      240
```

| | | | | | | | | | | | | | | | | |
|---|---|---|---|---|---|---|---|---|---|---|---|---|---|---|---|---|
| CTG | AAT | AAT | GAA | ACC | AGA | CCC | AGT | GTT | CAA | GAG | GAC | TCA | CAA | GCC | TTC | 769 |
| Leu | Asn | Asn | Glu | Thr 245 | Arg | Pro | Ser | Val | Gln 250 | Glu | Asp | Ser | Gln | Ala 255 | Phe | |
| AAT | CCT | GAT | AAT | CCT | TAT | CAT | CAG | CAG | GAA | GGG | GAA | AGC | ATG | ACA | TTC | 817 |
| Asn | Pro | Asp | Asn | Pro 260 | Tyr | His | Gln | Gln | Glu 265 | Gly | Glu | Ser | Met | Thr 270 | Phe | |
| GAC | CCT | AGA | CTG | GAT | CAC | GAA | GGA | ATC | TGT | TGT | ATA | GAA | TGT | AGG | CGG | 865 |
| Asp | Pro | Arg 275 | Leu | Asp | His | Glu | Gly 280 | Ile | Cys | Cys | Ile | Glu 285 | Cys | Arg | Arg | |
| AGC | TAC | ACC | CAC | TGC | CAG | AAG | ATC | TGT | GAA | CCC | CTG | GGG | GGC | TAT | TAC | 913 |
| Ser | Tyr | Thr 290 | His | Cys | Gln | Lys 295 | Ile | Cys | Glu | Pro | Leu 300 | Gly | Gly | Tyr | Tyr | |
| CCA | TGG | CCT | TAT | AAT | TAT | CAA | GGC | TGC | CGT | TCG | GCC | TGC | AGA | GTC | ATC | 961 |
| Pro 305 | Trp | Pro | Tyr | Asn | Tyr 310 | Gln | Gly | Cys | Arg | Ser 315 | Ala | Cys | Arg | Val | Ile 320 | |
| ATG | CCA | TGT | AGC | TGG | TGG | GTG | GCC | CGT | ATC | TTG | GGC | ATG | GTG | TGA | | 1006 |
| Met | Pro | Cys | Ser | Trp 325 | Trp | Val | Ala | Arg | Ile 330 | Leu | Gly | Met | Val | Stop 335 | | |

( 2 ) INFORMATION FOR SEQ ID NO:6:

( i ) SEQUENCE CHARACTERISTICS:
        ( A ) LENGTH: 1006 base pairs
        ( B ) TYPE: nucleic acid
        ( C ) STRANDEDNESS: double
        ( D ) TOPOLOGY: linear ( v i ) ORIGINAL SOURCE:
        ( A ) ORGANISM: Human being (Homo Sapiens)

( i x ) FEATURE:
        ( A ) NAME/KEY: P CDS
        ( B ) LOCATION: 2 .. 1003
        ( C ) IDENTIFICATION METHOD: E ( x i ) SEQUENCE DESCRIPTION: SEQ ID NO:6:

| | | | | | | | | | | | | | | | | |
|---|---|---|---|---|---|---|---|---|---|---|---|---|---|---|---|---|
| C | ATG | ACA | GAG | AAC | TCC | GAC | AAA | GTT | CCC | ATT | GCC | CTG | GTG | GGA | CCT GAT | 49 |
| | Met | Thr | Glu | Asn 5 | Ser | Asp | Lys | Val | Pro 10 | Ile | Ala | Leu | Val | Gly 15 | Pro Asp | |
| GAC | GTG | GAA | TTC | TGC | AGC | CCC | CCG | GCG | TAC | GCT | ACG | CTG | ACG | GTG | AAG | 97 |
| Asp | Val | Glu | Phe 20 | Cys | Ser | Pro | Pro | Ala 25 | Tyr | Ala | Thr | Leu | Thr 30 | Val | Lys | |
| CCC | TCC | AGC | CCC | GCG | CGG | CTG | CTC | AAG | GTG | GGA | GCC | GTG | GTC | CTC | ATT | 145 |
| Pro | Ser | Ser 35 | Pro | Ala | Arg | Leu | Leu 40 | Lys | Val | Gly | Ala | Val 45 | Val | Leu | Ile | |
| TCG | GGA | GCT | GTG | CTG | CTG | CTC | TTT | GGG | GCC | ATC | GGG | GCC | TTC | TAC | TTC | 193 |
| Ser | Gly 50 | Ala | Val | Leu | Leu | Leu 55 | Phe | Gly | Ala | Ile | Gly 60 | Ala | Phe | Tyr | Phe | |
| TGG | AAG | GGG | AGC | GAC | AGT | CAC | ATT | TAC | AAT | GTC | CAT | TAC | ACC | ATG | AGT | 241 |
| Trp 65 | Lys | Gly | Ser | Asp | Ser 70 | His | Ile | Tyr | Asn | Val 75 | His | Tyr | Thr | Met | Ser 80 | |
| ATC | AAT | GGG | AAA | CTA | CAA | GAT | GGG | TCA | ATG | GAA | ATA | GAC | GCT | GGG | AAC | 289 |
| Ile | Asn | Gly | Lys | Leu 85 | Gln | Asp | Gly | Ser | Met 90 | Glu | Ile | Asp | Ala | Gly 95 | Asn | |
| AAC | TTG | GAG | ACC | TTT | AAA | ATG | GGA | AGT | GGA | GCT | GAA | GAA | GCA | ATT | GCA | 337 |
| Asn | Leu | Glu | Thr 100 | Phe | Lys | Met | Gly | Ser 105 | Gly | Ala | Glu | Glu | Ala 110 | Ile | Ala | |
| GTT | AAT | GAT | TTC | CAG | AAT | GGC | ATC | ACA | GGA | ATT | CGT | TTT | GCT | GGA | GGA | 385 |
| Val | Asn | Asp | Phe 115 | Gln | Asn | Gly | Ile | Thr 120 | Gly | Ile | Arg | Phe | Ala 125 | Gly | Gly | |
| GAG | AAG | TGC | TAC | ATT | AAA | GCG | CAA | GTG | AAG | GCT | CGT | ATT | CCT | GAG | GTG | 433 |
| Glu | Lys | Cys 130 | Tyr | Ile | Lys | Ala | Gln 135 | Val | Lys | Ala | Arg | Ile 140 | Pro | Glu | Val | |
| GGC | GCC | GTG | ACC | AAA | CAG | AGC | ATC | TCC | TCC | AAA | CTG | GAA | GGC | AAG | ATC | 481 |

|   |   |   |   |   |   |   |   |   |   |   |   |   |   |   |   |
|---|---|---|---|---|---|---|---|---|---|---|---|---|---|---|---|
| Gly | Ala | Val | Thr | Lys | Gln | Ser | Ile | Ser | Ser | Lys | Leu | Glu | Gly | Lys | Ile |
| 145 |   |   |   |   | 150 |   |   |   | 155 |   |   |   |   |   | 160 |

| ATG | CCA | GTC | AAA | TAT | GAA | GAA | AAT | TCT | CTT | ATC | TGG | GTG | GCT | GTA | GAT | 529 |
|---|---|---|---|---|---|---|---|---|---|---|---|---|---|---|---|---|
| Met | Pro | Val | Lys | Tyr | Glu | Glu | Asn | Ser | Leu | Ile | Trp | Val | Ala | Val | Asp |  |
|   |   |   |   | 165 |   |   |   |   | 170 |   |   |   |   | 175 |   |  |

| CAG | CCT | GTG | AAG | GAC | AAC | AGC | TTC | TTG | AAT | TCT | AAG | GTG | TTA | GAA | CTC | 577 |
|---|---|---|---|---|---|---|---|---|---|---|---|---|---|---|---|---|
| Gln | Pro | Val | Lys | Asp | Asn | Ser | Phe | Leu | Asn | Ser | Lys | Val | Leu | Glu | Leu |  |
|   |   |   | 180 |   |   |   |   | 185 |   |   |   |   | 190 |   |   |  |

| TGC | GGT | GAC | CTT | CCT | ATT | TTC | TGG | CTT | AAA | CCA | ACC | TAT | CCA | AAA | GAA | 625 |
|---|---|---|---|---|---|---|---|---|---|---|---|---|---|---|---|---|
| Cys | Gly | Asp | Leu | Pro | Ile | Phe | Trp | Leu | Lys | Pro | Thr | Tyr | Pro | Lys | Glu |  |
|   |   | 195 |   |   |   |   | 200 |   |   |   |   | 205 |   |   |   |  |

| ATC | CAG | AGG | GAA | AGA | AGA | GAA | GTG | GTA | AGA | AAA | ATT | GTT | CCA | ACT | ACC | 673 |
|---|---|---|---|---|---|---|---|---|---|---|---|---|---|---|---|---|
| Ile | Gln | Arg | Glu | Arg | Arg | Glu | Val | Val | Arg | Lys | Ile | Val | Pro | Thr | Thr |  |
|   | 210 |   |   |   |   | 215 |   |   |   |   | 220 |   |   |   |   |  |

| ACA | AAA | AGA | CCA | CAC | AGT | GGA | CCA | CGG | AGC | AAC | CCA | GGC | GCT | GGA | AGA | 721 |
|---|---|---|---|---|---|---|---|---|---|---|---|---|---|---|---|---|
| Thr | Lys | Arg | Pro | His | Ser | Gly | Pro | Arg | Ser | Asn | Pro | Gly | Ala | Gly | Arg |  |
| 225 |   |   |   |   | 230 |   |   |   |   | 235 |   |   |   |   | 240 |  |

| CTG | AAT | AAT | GAA | ACC | AGA | CCC | AGT | GTT | CAA | GAG | GAC | TCA | CAA | GCC | TTC | 769 |
|---|---|---|---|---|---|---|---|---|---|---|---|---|---|---|---|---|
| Leu | Asn | Asn | Glu | Thr | Arg | Pro | Ser | Val | Gln | Glu | Asp | Ser | Gln | Ala | Phe |  |
|   |   |   |   | 245 |   |   |   |   | 250 |   |   |   |   | 255 |   |  |

| AAT | CCT | GAT | AAT | CCT | TAT | CAT | CAG | CAG | GAA | GGG | GAA | AGC | ATG | ACA | TTC | 817 |
|---|---|---|---|---|---|---|---|---|---|---|---|---|---|---|---|---|
| Asn | Pro | Asp | Asn | Pro | Tyr | His | Gln | Gln | Glu | Gly | Glu | Ser | Met | Thr | Phe |  |
|   |   |   | 260 |   |   |   |   | 265 |   |   |   |   | 270 |   |   |  |

| GAC | CCT | AGA | CTG | GAT | CAC | GAA | GGA | ATC | TGT | TGT | ATA | GAA | TGT | AGG | CGG | 865 |
|---|---|---|---|---|---|---|---|---|---|---|---|---|---|---|---|---|
| Asp | Pro | Arg | Leu | Asp | His | Glu | Gly | Ile | Cys | Cys | Ile | Glu | Cys | Arg | Arg |  |
|   |   | 275 |   |   |   |   | 280 |   |   |   |   | 285 |   |   |   |  |

| AGC | TAC | ACC | CAC | TGC | CAG | AAG | ATC | TGT | GAA | CCC | CTG | GGG | GGC | TAT | TAC | 913 |
|---|---|---|---|---|---|---|---|---|---|---|---|---|---|---|---|---|
| Ser | Tyr | Thr | His | Cys | Gln | Lys | Ile | Cys | Glu | Pro | Leu | Gly | Gly | Tyr | Tyr |  |
|   | 290 |   |   |   |   | 295 |   |   |   |   | 300 |   |   |   |   |  |

| CCA | TGG | CCT | TAT | AAT | TAT | CAA | GGC | TGC | CGT | TCG | GCC | TGC | AGA | GTC | ATC | 961 |
|---|---|---|---|---|---|---|---|---|---|---|---|---|---|---|---|---|
| Pro | Trp | Pro | Tyr | Asn | Tyr | Gln | Gly | Cys | Arg | Ser | Ala | Cys | Arg | Val | Ile |  |
| 305 |   |   |   |   | 310 |   |   |   |   | 315 |   |   |   |   | 320 |  |

| ATG | CCA | TGT | AGC | TGG | TGG | GTG | GCC | CGT | ATC | TTG | GGC | ATG | GTG | TGA |   | 1006 |
|---|---|---|---|---|---|---|---|---|---|---|---|---|---|---|---|---|
| Met | Pro | Cys | Ser | Trp | Trp | Val | Ala | Arg | Ile | Leu | Gly | Met | Val | Stop |   |  |
|   |   |   |   | 325 |   |   |   |   | 330 |   |   |   | 335 |   |   |  |

( 2 ) INFORMATION FOR SEQ ID NO:7:

( i ) SEQUENCE CHARACTERISTICS:
        ( A ) LENGTH: 892 base pairs
        ( B ) TYPE: nucleic acid
        ( C ) STRANDEDNESS: double
        ( D ) TOPOLOGY: linear ( v i ) ORIGINAL SOURCE:
        ( A ) ORGANISM: Human being (Homo Sapiens)

( i x ) FEATURE:
        ( A ) NAME/KEY: P CDS
        ( B ) LOCATION: 2 .. 889
        ( C ) IDENTIFICATION METHOD: E ( x i ) SEQUENCE DESCRIPTION: SEQ ID NO:7:

| C | ATG | ACA | GAG | AAC | TCC | GAC | AAA | GTT | CCC | ATT | GCC | CTG | GTG | GGA | CCT | GAT | 49 |
|---|---|---|---|---|---|---|---|---|---|---|---|---|---|---|---|---|---|
|   | Met | Thr | Glu | Asn | Ser | Asp | Lys | Val | Pro | Ile | Ala | Leu | Val | Gly | Pro | Asp |  |
|   | 1 |   |   |   | 5 |   |   |   |   | 10 |   |   |   |   | 15 |   |  |

| GAC | GTG | GAA | TTC | TGC | AGC | CCC | CCG | GCG | TAC | GCT | ACG | CTG | ACG | GTG | AAG | 97 |
|---|---|---|---|---|---|---|---|---|---|---|---|---|---|---|---|---|
| Asp | Val | Glu | Phe | Cys | Ser | Pro | Pro | Ala | Tyr | Ala | Thr | Leu | Thr | Val | Lys |  |
|   |   |   | 20 |   |   |   |   | 25 |   |   |   |   | 30 |   |   |  |

| CCC | TCC | AGC | CCC | GCG | CGG | CTG | CTC | AAG | GTG | GGA | GCC | GTG | GTC | CTC | ATT | 145 |
|---|---|---|---|---|---|---|---|---|---|---|---|---|---|---|---|---|
| Pro | Ser | Ser | Pro | Ala | Arg | Leu | Leu | Lys | Val | Gly | Ala | Val | Val | Leu | Ile |  |
|   |   | 35 |   |   |   |   | 40 |   |   |   |   | 45 |   |   |   |  |

| TCG | GGA | GCT | GTG | CTG | CTG | CTC | TTT | GGG | GCC | ATC | GGG | GCC | TTC | TAC | TTC | 193 |
|---|---|---|---|---|---|---|---|---|---|---|---|---|---|---|---|---|
| Ser | Gly | Ala | Val | Leu | Leu | Leu | Phe | Gly | Ala | Ile | Gly | Ala | Phe | Tyr | Phe |  |

| | | | | | | | | | | | | | | | | |
|---|---|---|---|---|---|---|---|---|---|---|---|---|---|---|---|---|
| | | 50 | | | | | 55 | | | | | 60 | | | | |
| TGG | AAG | GGG | AGC | GAC | AGT | CAC | ATT | TAC | AAT | GTC | CAT | TAC | ACC | ATG | AGT | 241 |
| Trp | Lys | Gly | Ser | Asp | Ser | His | Ile | Tyr | Asn | Val | His | Tyr | Thr | Met | Ser | |
| 65 | | | | | 70 | | | | | 75 | | | | | 80 | |
| ATC | AAT | GGG | AAA | TTA | CAA | GAT | GGG | TCA | ATG | GAA | ATA | GAC | GCT | GGG | AAC | 289 |
| Ile | Asn | Gly | Lys | Leu | Gln | Asp | Gly | Ser | Met | Glu | Ile | Asp | Ala | Gly | Asn | |
| | | | | 85 | | | | | 90 | | | | | 95 | | |
| AAC | TTG | GAG | ACC | TTT | AAA | ATG | GGA | AGT | GGA | GCT | GAA | GAA | GCA | ATT | GCA | 337 |
| Asn | Leu | Glu | Thr | Phe | Lys | Met | Gly | Ser | Gly | Ala | Glu | Glu | Ala | Ile | Ala | |
| | | | 100 | | | | | 105 | | | | | 110 | | | |
| GTT | AAT | GAT | TTC | CAG | AAT | GAA | GGC | AAG | ATC | ATG | CCA | GTC | AAA | TAT | GAA | 385 |
| Val | Asn | Asp | Phe | Gln | Asn | Glu | Gly | Lys | Ile | Met | Pro | Val | Lys | Tyr | Glu | |
| | | 115 | | | | | 120 | | | | | 125 | | | | |
| GAA | AAT | TCT | CTT | ATC | TGG | GTG | GCT | GTA | GAT | CAG | CCT | GTG | AAG | GAC | AAC | 433 |
| Glu | Asn | Ser | Leu | Ile | Trp | Val | Ala | Val | Asp | Gln | Pro | Val | Lys | Asp | Asn | |
| | 130 | | | | | 135 | | | | | 140 | | | | | |
| AGC | TTC | TTG | AGT | TCT | AAG | GTG | TTA | GAA | CTC | TGC | GGT | GAC | CTT | CCT | ATT | 481 |
| Ser | Phe | Leu | Ser | Ser | Lys | Val | Leu | Glu | Leu | Cys | Gly | Asp | Leu | Pro | Ile | |
| 145 | | | | | 150 | | | | | 155 | | | | | 160 | |
| TCC | TGG | CTT | AAA | CCA | ACC | TAT | CCA | AAA | GAA | ATC | CAG | AGG | GAA | AGA | AGA | 529 |
| Ser | Trp | Leu | Lys | Pro | Thr | Tyr | Pro | Lys | Glu | Ile | Gln | Arg | Glu | Arg | Arg | |
| | | | | 165 | | | | | 170 | | | | | 175 | | |
| GAA | GTG | GTA | AGA | AAA | ATT | GTT | CCA | ACT | ACC | ACA | AAA | AGA | CCA | CAC | AAT | 577 |
| Glu | Val | Val | Arg | Lys | Ile | Val | Pro | Thr | Thr | Thr | Lys | Arg | Pro | His | Asn | |
| | | | 180 | | | | | 185 | | | | | 190 | | | |
| GGA | CCA | CGG | AGC | AAC | CCA | GGC | GCT | GGA | AGA | CTG | AAT | AAT | GAA | ACC | AGA | 625 |
| Gly | Pro | Arg | Ser | Asn | Pro | Gly | Ala | Gly | Arg | Leu | Asn | Asn | Glu | Thr | Arg | |
| | | 195 | | | | | 200 | | | | | 205 | | | | |
| CCC | AGT | GTT | CAA | GAG | GAC | TCA | CAA | GCC | TTC | AAT | CCT | GAT | AAT | CCT | TAT | 673 |
| Pro | Ser | Val | Gln | Glu | Asp | Ser | Gln | Ala | Phe | Asn | Pro | Asp | Asn | Pro | Tyr | |
| | 210 | | | | | 215 | | | | | 220 | | | | | |
| CAT | CAG | CAG | GAA | GGG | GAA | AGC | ATG | ACA | TTC | GAC | CCT | AGA | CTG | GAT | CAC | 721 |
| His | Gln | Gln | Glu | Gly | Glu | Ser | Met | Thr | Phe | Asp | Pro | Arg | Leu | Asp | His | |
| 225 | | | | | 230 | | | | | 235 | | | | | 240 | |
| GAA | GGA | ATC | TGT | TGT | ATA | GAA | TGT | AGG | CGG | AGC | TAC | ACC | CAC | TGC | CAG | 769 |
| Glu | Gly | Ile | Cys | Cys | Ile | Glu | Cys | Arg | Arg | Ser | Tyr | Thr | His | Cys | Gln | |
| | | | | 245 | | | | | 250 | | | | | 255 | | |
| AAG | ATC | TGT | GAA | CCC | CTG | GGG | GGC | TAT | TAC | CCA | TGG | CCT | TAT | AAT | TAT | 817 |
| Lys | Ile | Cys | Glu | Pro | Leu | Gly | Gly | Tyr | Tyr | Pro | Trp | Pro | Tyr | Asn | Tyr | |
| | | | 260 | | | | | 265 | | | | | 270 | | | |
| CAA | GGC | TGC | CGT | TCG | GCC | TGC | AGA | GTC | ATC | ATG | CCA | TGT | AGC | TGG | TGG | 865 |
| Gln | Gly | Cys | Arg | Ser | Ala | Cys | Arg | Val | Ile | Met | Pro | Cys | Ser | Trp | Trp | |
| | | 275 | | | | | 280 | | | | | 285 | | | | |
| GTG | GCC | CGT | ATC | TTG | GGC | ATG | GTG | TGA | | | | | | | | 892 |
| Val | Ala | Arg | Ile | Leu | Gly | Met | Val | Stop | | | | | | | | |
| | 290 | | | | | 295 | | | | | | | | | | |

( 2 ) INFORMATION FOR SEQ ID NO:8:

( i ) SEQUENCE CHARACTERISTICS:
        ( A ) LENGTH: 27 base pairs
        ( B ) TYPE: nucleic acid
        ( C ) STRANDEDNESS: double
        ( D ) TOPOLOGY: linear ( v i ) ORIGINAL SOURCE:
        ( A ) ORGANISM: Human being (Homo Sapiens)

( v i i ) IMMEDIATE SOURCE:
        ( B ) CLONE: phCHM-ILAST8

( i x ) FEATURE:
        ( A ) NAME/KEY: P CDS
        ( B ) LOCATION: 1 ... 27

(C) IDENTIFICATION METHOD: E (xi) SEQUENCE DESCRIPTION: SEQ ID NO:8:

| GTG | GCC | CGT | ATC | TTG | GGC | ATG | GTG | TGA | 27 |
|-----|-----|-----|-----|-----|-----|-----|-----|-----|----|
| Val | Ala | Arg | Ile | Leu | Gly | Met | Val | Stop | |
| 1 | | | | 5 | | | | | |

(2) INFORMATION FOR SEQ ID NO:9:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Other nucleic acid, Synthetic DNA (xi) SEQUENCE DESCRIPTION: SEQ ID NO:9:

GTAAAACGAC GGCCAGT                          17

(2) INFORMATION FOR SEQ ID NO:10:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Other nucleic acid, Synthetic DNA (xi) SEQUENCE DESCRIPTION: SEQ ID NO:10:

CAGGAAACAG CTATGAC                          17

(2) INFORMATION FOR SEQ ID NO:11:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: Other nucleic acid, Synthetic DNA (xi) SEQUENCE DESCRIPTION: SEQ ID NO:11:

CTCGAGGCCA TGGCGGCCGC TTTTTTTTTT TTTTTTTTTT TTTTTTTTTT TTTTTTTTTT    60

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Other nucleic acid, Synthetic DNA (xi) SEQUENCE DESCRIPTION: SEQ ID NO:12:

GCGGCCGCCA TGGCCTCGAG                        20

(2) INFORMATION FOR SEQ ID NO:13:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: Other nucleic acid, Synthetic DNA (xi) SEQUENCE DESCRIPTION: SEQ ID NO:13:

```
AGTCTCCAAG TGCCTCACT                                                        19
```

( 2 ) INFORMATION FOR SEQ ID NO:14:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: Other nucleic acid, Synthetic DNA ( x i ) SEQUENCE DESCRIPTION: SEQ ID NO:14:

```
CGAGGCCATG GCGGCC                                                           16
```

( 2 ) INFORMATION FOR SEQ ID NO:15:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Other nucleic acid, Synthetic DNA ( x i ) SEQUENCE DESCRIPTION: SEQ ID NO:15:

```
CATGACAGAG AACTCCGA                                                         18
```

( 2 ) INFORMATION FOR SEQ ID NO:16:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Other nucleic acid, Synthetic DNA ( x i ) SEQUENCE DESCRIPTION: SEQ ID NO:16:

```
ACACCATGCC CAGGATGC                                                         18
```

( 2 ) INFORMATION FOR SEQ ID NO:17:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: Other nucleic acid, Synthetic DNA ( x i ) SEQUENCE DESCRIPTION: SEQ ID NO:17:

```
CCCTAGACTG GATCAC                                                           16
```

( 2 ) INFORMATION FOR SEQ ID NO:18:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: Other nucleic acid, Synthetic DNA ( x i ) SEQUENCE DESCRIPTION: SEQ ID NO:18:

```
TCACACCATG CCCAAGATAC GGGCCAC                                               27
```

( 2 ) INFORMATION FOR SEQ ID NO:19:

(i) SEQUENCE CHARACTERISTICS:
(A) LENGTH: 334 amino acids
(B) TYPE: amino acid
(C) STRANDEDNESS: single
(D) TOPOLOGY: linear (xi) SEQUENCE DESCRIPTION: SEQ ID NO:19:

```
Met Thr Glu Asn Ser Asp Lys Val Pro Ile Ala Leu Val Gly Pro Asp
 1               5                  10                  15
Asp Val Glu Phe Cys Ser Pro Ala Tyr Ala Thr Leu Thr Val Lys
                20                  25                  30
Pro Ser Ser Pro Ala Arg Leu Leu Lys Val Gly Ala Val Val Leu Ile
            35                  40                  45
Ser Gly Ala Val Leu Leu Leu Phe Gly Ala Ile Gly Ala Phe Tyr Phe
    50                  55                  60
Trp Lys Gly Ser Asp Ser His Ile Tyr Asn Val His Tyr Thr Met Ser
65                  70                  75                  80
Ile Asn Gly Lys Leu Gln Asp Gly Ser Met Glu Ile Asp Ala Gly Asn
                85                  90                  95
Asn Leu Glu Thr Phe Lys Met Gly Ser Gly Ala Glu Ala Ile Ala
                100                 105                 110
Val Asn Asp Phe Gln Asn Gly Ile Thr Gly Ile Arg Phe Ala Gly Gly
            115                 120                 125
Glu Lys Cys Tyr Ile Lys Ala Gln Val Lys Ala Arg Ile Pro Glu Val
    130                 135                 140
Gly Ala Val Thr Lys Gln Ser Ile Ser Ser Lys Leu Glu Gly Lys Ile
145                 150                 155                 160
Met Pro Val Lys Tyr Glu Glu Asn Ser Leu Ile Trp Val Ala Val Asp
                165                 170                 175
Gln Pro Val Lys Asp Asn Ser Phe Leu Ser Ser Lys Val Leu Glu Leu
            180                 185                 190
Cys Gly Asp Leu Pro Ile Phe Trp Leu Lys Pro Thr Tyr Pro Lys Glu
    195                 200                 205
Ile Gln Arg Glu Arg Arg Glu Val Val Arg Lys Ile Val Pro Thr Thr
210                 215                 220
Thr Lys Arg Pro His Ser Gly Pro Arg Ser Asn Pro Gly Ala Gly Arg
225                 230                 235                 240
Leu Asn Asn Glu Thr Arg Pro Ser Val Gln Glu Asp Ser Gln Ala Phe
                245                 250                 255
Asn Pro Asp Asn Pro Tyr His Gln Gln Glu Gly Glu Ser Met Thr Phe
            260                 265                 270
Asp Pro Arg Leu Asp His Glu Gly Ile Cys Cys Ile Glu Cys Arg Arg
    275                 280                 285
Ser Tyr Thr His Cys Gln Lys Ile Cys Glu Pro Leu Gly Gly Tyr Tyr
290                 295                 300
Pro Trp Pro Tyr Asn Tyr Gln Gly Cys Arg Ser Ala Cys Arg Val Ile
305                 310                 315                 320
Met Pro Cys Ser Trp Trp Val Ala Arg Ile Leu Gly Met Val
                325                 330
```

(2) INFORMATION FOR SEQ ID NO:20:

(i) SEQUENCE CHARACTERISTICS:
(A) LENGTH: 334 amino acids
(B) TYPE: amino acid
(C) STRANDEDNESS: single
(D) TOPOLOGY: linear ( x i ) SEQUENCE DESCRIPTION: SEQ ID NO:20:

| Met | Thr | Glu | Asn | Ser | Asp | Lys | Val | Pro | Ile | Ala | Leu | Val | Gly | Pro | Asp |
|---|---|---|---|---|---|---|---|---|---|---|---|---|---|---|---|
| 1 | | | | 5 | | | | | 10 | | | | | 15 | |

| Asp | Val | Glu | Phe | Cys | Ser | Pro | Pro | Ala | Tyr | Ala | Thr | Leu | Thr | Val | Lys |
|---|---|---|---|---|---|---|---|---|---|---|---|---|---|---|---|
| | | | 20 | | | | | 25 | | | | | 30 | | |

| Pro | Ser | Ser | Pro | Ala | Arg | Leu | Leu | Lys | Val | Gly | Ala | Val | Val | Leu | Ile |
| | | 35 | | | | | 40 | | | | | 45 | | | |

| Ser | Gly | Ala | Val | Leu | Leu | Leu | Phe | Gly | Ala | Ile | Gly | Ala | Phe | Tyr | Phe |
| | 50 | | | | | 55 | | | | | 60 | | | | |

| Trp | Lys | Gly | Ser | Asp | Ser | His | Ile | Tyr | Asn | Val | His | Tyr | Thr | Met | Ser |
| 65 | | | | | 70 | | | | | 75 | | | | | 80 |

| Ile | Asn | Gly | Lys | Leu | Gln | Asp | Gly | Ser | Met | Glu | Ile | Asp | Ala | Gly | Asn |
| | | | | 85 | | | | | 90 | | | | | 95 | |

| Asn | Leu | Glu | Thr | Phe | Lys | Met | Gly | Ser | Gly | Ala | Glu | Glu | Ala | Ile | Ala |
| | | | 100 | | | | | 105 | | | | | 110 | | |

| Val | Asn | Asp | Phe | Gln | Asn | Gly | Ile | Thr | Gly | Ile | Arg | Phe | Ala | Gly | Gly |
| | | 115 | | | | | 120 | | | | | 125 | | | |

| Glu | Lys | Cys | Tyr | Ile | Lys | Ala | Gln | Val | Lys | Ala | Arg | Ile | Pro | Glu | Val |
| | 130 | | | | | 135 | | | | | 140 | | | | |

| Gly | Ala | Val | Thr | Lys | Gln | Ser | Ile | Ser | Ser | Lys | Leu | Glu | Gly | Lys | Ile |
| 145 | | | | | 150 | | | | | 155 | | | | | 160 |

| Met | Pro | Val | Lys | Tyr | Glu | Glu | Asn | Ser | Leu | Ile | Trp | Val | Ala | Val | Asp |
| | | | | 165 | | | | | 170 | | | | | 175 | |

| Gln | Pro | Val | Lys | Asp | Asn | Ser | Phe | Leu | Asn | Ser | Lys | Val | Leu | Glu | Leu |
| | | | 180 | | | | | 185 | | | | | 190 | | |

| Cys | Gly | Asp | Leu | Pro | Ile | Phe | Trp | Leu | Lys | Pro | Thr | Tyr | Pro | Lys | Glu |
| | | 195 | | | | | 200 | | | | | 205 | | | |

| Ile | Gln | Arg | Glu | Arg | Arg | Glu | Val | Val | Arg | Lys | Ile | Val | Pro | Thr | Thr |
| | 210 | | | | | 215 | | | | | 220 | | | | |

| Thr | Lys | Arg | Pro | His | Ser | Gly | Pro | Arg | Ser | Asn | Pro | Gly | Ala | Gly | Arg |
| 225 | | | | | 230 | | | | | 235 | | | | | 240 |

| Leu | Asn | Asn | Glu | Thr | Arg | Pro | Ser | Val | Gln | Glu | Asp | Ser | Gln | Ala | Phe |
| | | | | 245 | | | | | 250 | | | | | 255 | |

| Asn | Pro | Asp | Asn | Pro | Tyr | His | Gln | Gln | Glu | Gly | Glu | Ser | Met | Thr | Phe |
| | | | 260 | | | | | 265 | | | | | 270 | | |

| Asp | Pro | Arg | Leu | Asp | His | Glu | Gly | Ile | Cys | Cys | Ile | Glu | Cys | Arg | Arg |
| | | 275 | | | | | 280 | | | | | 285 | | | |

| Ser | Tyr | Thr | His | Cys | Gln | Lys | Ile | Cys | Glu | Pro | Leu | Gly | Gly | Tyr | Tyr |
| | 290 | | | | | 295 | | | | | 300 | | | | |

| Pro | Trp | Pro | Tyr | Asn | Tyr | Gln | Gly | Cys | Arg | Ser | Ala | Cys | Arg | Val | Ile |
| 305 | | | | | 310 | | | | | 315 | | | | | 320 |

| Met | Pro | Cys | Ser | Trp | Trp | Val | Ala | Arg | Ile | Leu | Gly | Met | Val | | |
| | | | | 325 | | | | | 330 | | | | | | |

( 2 ) INFORMATION FOR SEQ ID NO:21:

( i ) SEQUENCE CHARACTERISTICS:
        ( A ) LENGTH: 296 amino acids
        ( B ) TYPE: amino acid
        ( C ) STRANDEDNESS: single
        ( D ) TOPOLOGY: linear ( x i ) SEQUENCE DESCRIPTION: SEQ ID NO:21:

| Met | Thr | Glu | Asn | Ser | Asp | Lys | Val | Pro | Ile | Ala | Leu | Val | Gly | Pro | Asp |
|---|---|---|---|---|---|---|---|---|---|---|---|---|---|---|---|
| 1 | | | | 5 | | | | | 10 | | | | | 15 | |

| | | | | | | | | | | | | | | |
|---|---|---|---|---|---|---|---|---|---|---|---|---|---|---|
| Asp | Val | Glu | Phe 20 | Cys | Ser | Pro | Pro | Ala 25 | Tyr | Ala | Thr | Leu | Thr 30 | Val | Lys |
| Pro | Ser | Ser 35 | Pro | Ala | Arg | Leu | Leu 40 | Lys | Val | Gly | Ala | Val 45 | Val | Leu | Ile |
| Ser | Gly 50 | Ala | Val | Leu | Leu | Leu 55 | Phe | Gly | Ala | Ile | Gly 60 | Ala | Phe | Tyr | Phe |
| Trp 65 | Lys | Gly | Ser | Asp | Ser 70 | His | Ile | Tyr | Asn | Val 75 | His | Tyr | Thr | Met | Ser 80 |
| Ile | Asn | Gly | Lys | Leu 85 | Gln | Asp | Gly | Ser | Met 90 | Glu | Ile | Asp | Ala | Gly 95 | Asn |
| Asn | Leu | Glu | Thr 100 | Phe | Lys | Met | Gly | Ser 105 | Gly | Ala | Glu | Glu | Ala 110 | Ile | Ala |
| Val | Asn | Asp 115 | Phe | Gln | Asn | Glu | Gly 120 | Lys | Ile | Met | Pro | Val 125 | Lys | Tyr | Glu |
| Glu | Asn 130 | Ser | Leu | Ile | Trp | Val 135 | Ala | Val | Asp | Gln | Pro 140 | Val | Lys | Asp | Asn |
| Ser 145 | Phe | Leu | Ser | Ser | Lys 150 | Val | Leu | Glu | Leu | Cys 155 | Gly | Asp | Leu | Pro | Ile 160 |
| Ser | Trp | Leu | Lys | Pro 165 | Thr | Tyr | Pro | Lys | Glu 170 | Ile | Gln | Arg | Glu | Arg 175 | Arg |
| Glu | Val | Val | Arg 180 | Lys | Ile | Val | Pro | Thr 185 | Thr | Thr | Lys | Arg | Pro 190 | His | Asn |
| Gly | Pro | Arg 195 | Ser | Asn | Pro | Gly | Ala 200 | Gly | Arg | Leu | Asn | Asn 205 | Glu | Thr | Arg |
| Pro | Ser 210 | Val | Gln | Glu | Asp | Ser 215 | Gln | Ala | Phe | Asn | Pro 220 | Asp | Asn | Pro | Tyr |
| His 225 | Gln | Gln | Glu | Gly | Glu 230 | Ser | Met | Thr | Phe | Asp 235 | Pro | Arg | Leu | Asp | His 240 |
| Glu | Gly | Ile | Cys | Cys 245 | Ile | Glu | Cys | Arg | Arg 250 | Ser | Tyr | Thr | His | Cys 255 | Gln |
| Lys | Ile | Cys | Glu 260 | Pro | Leu | Gly | Gly | Tyr 265 | Tyr | Pro | Trp | Pro | Tyr 270 | Asn | Tyr |
| Gln | Gly | Cys 275 | Arg | Ser | Ala | Cys | Arg 280 | Val | Ile | Met | Pro | Cys 285 | Ser | Trp | Trp |
| Val | Ala 290 | Arg | Ile | Leu | Gly | Met 295 | Val | | | | | | | | |

HUMAN CHONDROMODULIN-I PROTEIN

FIELD OF THE INVENTION

This invention relates to a novel human chondromodulin protein. More particularly, it relates to chondromodulin-I protein capable of stimulating the growth of chondrocytes in the presence or absence of fibroblast growth factor and promoting the differential potency of said cells, an isolated DNA (gene) encoding said protein, expression vectors containing said DNA, transformants capable of producing recombinant chondromodulin-I protein, a process for producing chondromodulin-I protein by culturing said transformants and a pharmaceutical composition containing chondromodulin-I protein as an active ingredient. The present invention also relates to the use of chondromodulin-I protein in the treatment of fracture and various cartilage diseases and as an anti-tumor drug.

BACKGROUND OF THE INVENTION

Almost all the bones of mammals, except for flat bones such as cranial bone and the like, are formed through a mechanism called "intracartilaginous ossification", which comprises expression of primordial chondrocytes during the embryonic stage, growth and differentiation of said cartilaginous cells, generation of primordial cartilages such as proteoglycan, collagen II, collagen IX collagen X and the like, infiltration of capillary vessels which is accompanied by the decomposition of ground substance of cartilage and progression of calcification around the vesicles of said ground substance, and the replacement thereof with bone as the final step. Thus, the cartilage metabolism plays a significantly important role in the bone-formation, especially in the elongation of a bone along the axis.

It has been known that a variety of hormones and growth factors participate in the bone-formation (osteogenesis) process, including insulin-like growth factor (IGF1, IGF2), fibroblast growth factor (FGF), growth hormone, transforming cell growth factor (TGF-β) and the like. It has also been suggested that a certain active factor exists in cartilage, which stimulates the growth and differentiation of chondrocytes. However, there have been no reports which disclose the purification of the factor to such an extent that a single band is obtained on SDS-PAGE, and its definite physiological activity has not been determined. Neame et al. [Peter J. Neame et al., Journal of Biological Chemistry Vol. 265, No. 17, 9628–9633, (1990)] reported that they separated from bovine cartilage a glycosylated protein having an amino acid sequence highly similar to that of chondromodulin in the course of their studies for the identification of constitutive proteins in cartilage. However, they still have not elucidated the biological functions of said glycosylated protein.

The protein which concerns the above-mentioned growth of chondrocytes and the like is known as chondromodulin protein having biological activities as illustrated below.

The expression of the growth and differentiation of chondrocytes plays an important role in the course of recovery from fracture or various cartilage diseases as follows: inflammatory reaction at the injured site, growth of the periost-derived cells, expression and growth of chondrocytes, synthesis of extra-cellular ground substances, calcification of said substances, and replacement thereof with bone tissues. As can be easily understood, the growth of cartilage tissue at the site of fracture is essential for the formation of bone tissue. Additionally, it is obvious that the growth of the chondrocytes is also important in the course of the recovery from cartilage diseases accompanied by cartilage destruction or injury. Furthermore, before the growth or metastasis of tumor cells, infiltration of blood vessels into tissues occurs for the supply of necessary energy to tumor cells, and therefor the inhibition of such a infiltration is thought to be effective for the prevention of growth or metastasis of tumor cells.

It has been reported that a gene encoding chondromodulin-I protein has been cloned from a cDNA library constructed from fetal bovine cartilage and expressed in animal cells. The expressed recombinant protein possesses activities equivalent to those of purified bovine chondromodulin-I protein. Hiraki et al., Biochemical and Biophysical Research Communications, 175, 971–977 (1991); and European Patent Publication No. 473,080. Throughout the present specification, the term "human chondromodulin-I protein" or "human chondromodulin-I" will be expressed by the abbreviation "hChM-I" in some cases.

To use the recombinant proteins in humans safely, it is necessary to evaluate its antigenicity in humans, which can be carried out by analyzing the structure of human chondromodulin-I gene and comparing the same with that of bovine chondromodulin gene. If any differences which can be antigenic are found, it is preferable to apply the recombinant chondromodulin-I after modifying the bovine-type chondromodulin-I gene to convert the recombinant bovine-type protein into human-type one having less antigenicity by means of genetic engineering. The preparation of human-type chondromodulin-I protein through extraction and purification from human chondrocytes is actually impossible with respect to costs and resources.

As can be seen from the above, it is desirable to obtain enough amount of chondromodulin protein capable of inhibiting the amplification of chondrocytes or infiltration of blood vessels, said protein being less antigenic in human, and thereby providing treatment methods effective on the above-mentioned diseases. However, industrial production of said protein from cartilage tissue has been extremely difficult and practical application of said protein has been hindered because of the lack of means to obtain the protein in a large amount.

SUMMARY OF THE INVENTION

The present inventors have studied extensively with the aim of producing a large amount of human chondromodulin protein by the use of recombinant DNA techniques and have now succeeded in the isolation of a novel protein, which belongs to a family of chondromodulin protein, useful for the establishment of the purpose of the invention, cloning of a gene (cDNA) encoding said protein, construction of an expression vector, transformation of heterogeneous cells, and production of recombinant protein by culturing the transformants. The present inventors also investigated physiological activities of thus obtained human chondromodulin-I protein and demonstrated that said protein possesses above-mentioned activities and are useful in the treatment of fracture, various cartilage diseases, cancers and the like and can be formulated into pharmaceutical compositions.

Thus, this invention provides a human chondromodulin-I protein, which is a water-soluble protein composed of one polypeptide, has a molecular weight of about 26,000 dalton on SDS-polyacrylamide gel electrophoresis and has abilities to stimulate the growth of chondrocytes in the presence or absence of fibroblast growth factor, to promote the differential potency of chondrocytes and to inhibit the growth of vascular endothelial cells. This invention also provides a DNA fragment which is amplified by the synthetic DNAs comprising the nucleotide sequence presented in SEQ ID NO: 15 and 16, respectively.

This invention further provides a DNA fragment which is amplified by the synthetic DNAs comprising the nucleotide sequence presented in SEQ ID NO: 15 and 16, respectively, or a fragment(s) thereof.

This invention also provides an isolated gene (DNA) encoding human chondromodulin-I protein and expression vectors containing sequences required for the expression of said gene, which comprise, at least, a promoter sequence, signal peptide-like sequence, DNA sequence encoding the chondromodulin-I protein, and a terminator sequence, if desired.

This invention further provides a transformant transformed by an expression vector of the invention and a process for producing human chondromodulin-I protein by culturing said transformation in an appropriate medium for the expression of the DNA encoding chondromodulin-I protein and recovering the chondromodulin-I protein from the resultant cultured broth.

This invention also provides the recombinant human chondromodulin-I protein products produced by the method of the present invention.

This invention also provides the use of human chondromodulin-I protein obtained according to the procedure of the invention in the treatment of fracture, various cartilage diseases and cancer.

DETAILED DESCRIPTION OF THE INVENTION

Purification of the novel human chondromodulin-I protein can be conducted by any of conventional procedures known to one of skill in the art. The chondromodulin-I protein was obtained and purified by isolating chondrocytes from human cartilage, culturing the cells, separating the supernatant from cultured broth by centrifugation, concentrating the supernatant by ultrafiltration, subjecting the concentrate to a molecular sieve chromatography on Sephacryl S1200 column, and purifying the resultant product repeatedly with YMC pack C4 chromatography while changing the elution conditions.

This method, however, has some drawbacks because of difficulty in securing a steady supply of a large quantity of human tissue. Alternatively, purified chondromodulin-I protein can be obtained, as is described in Examples below, by culturing cells transformed with hChM-I gene, separating the chondromodulin-I protein associated with albumin from other contaminating proteins in the cultured broth by means of Blue Sepharose column or the like, and purifying repeatedly by, for example, chromatography using YMC pack C4 column or the like while changing eluting conditions. Thus purified protein of the invention has a molecular weight of about 26,000 dalton on SDS-PAGE and has activities to stimulate the growth of chondrocytes in the presence or absence of fibroblast growth factor (FGF), to promote the differential potency of chondrocytes, and to inhibit the growth of vascular endothelial cells.

The amino acid sequence of the purified peptide was determined, which is provided in SEQ ID NO: 2, 3 or 4 and seperately in SEQ ID No. 19, 20 or 21, respectively.

The present inventors then isolated cDNA encoding chondromodulin-I protein, cloned said DNA and constructed expression vectors. A base sequence encoding the chondromodulin-I protein is provided in SEQ ID NO: 2, 3, 4, 5, 6 or 7. Among these sequences, those shown in SEQ ID NO: 2, 3 and 4 contain partly a base sequence(s) of bovine gene, as primers used in PCR have been made on the basis of bovine chondromodulin gene. They, however, fall within the scope of the invention because recombinant proteins expressed in transformants transformed with these DNAs showed no variations in amino acid sequence compared to that of hChM-I protein, indicating that they have the same utility and effect as hChM-I gene and are useful for purposes of the present invention.

Once the amino acid and DNA sequences of human chondromodulin-I protein are determined, it is easy to obtain active derivatives of human chondromodulin-I protein, which derivatives fall within the scope of the invention, by conventional methods, such as site specific mutation of DNA, which leads to the deletion, replacement, modification or addition of amino acids without changing the properties of human chondromodulin-I protein. Therefore, this invention also provides active recombinant human chondromodulin-I protein derivatives obtained by conventional methods. Thus, for purposes of the invention, as disclosed and claimed herein, the term human chondromodulin-I protein refers to both of naturally occurring human chondromodulin-I protein and recombinant human chondromodulin-I protein produced by the method of the invention.

A DNA fragment(s) encoding chondromodulin-I protein of the invention can be obtained in conventional manners using DNA libraries containing a gene encoding the protein as illustrated below.

Examples of the libraries usable are those prepared from RNA isolated from normal human cartilage or human chondrosarcoma or the like, including plasmid cDNA library, phage cDNA library, phage genomic library and the like.

In case of phage cDNA library, normal human cartilage or human chondrosarcoma tissue is pulverized in liquid nitrogen, homogenized in a solvent such as aqueous guanidium isothiocyatate solution, and precipitates of total RNA are seperated by cesium chloride equilibrium density gradient centrifugation according to the method of Chirgwin et al., Biochemistry, 18, 5294–5299 (1978). After the resultant total RNA is purified by phenol extraction and ethanol precipitation, it is further purified with chromatography using oligo(dT)cellulose column to isolate the objective poly(A)-containing mRNA (polyA$^+$ mRNA), i.e., mRNAs.

Single-stranded cDNA can be obtained by hybridizing mRNAs previously prepared with DNA primers such as those described in Nature, 329, 836–838 (1987), specifically, those consisting of DNAs shown in SEQ ID NO: 11 and 12, or with Oligo(dT) consisting of 12–18 deoxythymidines in the presence of reverse transcriptase. The single-stranded cDNA is converted into double-stranded cDNA by treating with Escherichia coli DNA polymerase I or E. coli DNA ligase, RNase H or the like in a conventional manner, which is then blunt-ended with T4 DNA polymerase. To both ends of the cDNA strand are added small DNA fragments such as EcoRI adapter with T4 DNA ligase to generate the same base sequences as those producible with the restriction enzyme.

Alternatively, a DNA having EcoRI restricted ends is also obtainable by treating the cDNA with methylase such as EcoRI methylase to protect inherent EcoRI restriction site (s), adding EcoRI linkers or the like to the both ends with T4 DNA ligase, and digesting with restriction enzyme EcoRI.

When another restriction site such as BamHI or the like is to be used as cloning site in vector, the series of procedures described above would be carried out using, for example, BamHI adapter, or BamHI methylase, BamHI linker, and restriction enzyme BamHI.

The cDNA strand having ends treated as mentioned above is then packaged into a commercially available λphage vector, for example, λZAP (PROMEGA Biotechs, Inc.) or pGEM2 (PROMEGA Biotechs, Inc.) at EcoRI site in a conventional manner to obtain recombinant λphage DNAs or recombinant plasmid DNAs.

The resultant λphage DNAs are used in the in vitro packaging by means of commercially available in vitro packaging kit such as Gigapack Gold (PROMEGA Biotechs, Inc.) to obtain λphage particles containing recombinant λphage DNA.

The resultant λphage particles are then transfected into host cells such as *E. coli* according to a conventional manner (Molecular Cloning, Cold Spring Harbor Laboratory, p. 85 (1982)) for amplification. Recombinant plasmid DNAs will be transformed into host cells such as *E. coli* in a conventional manner and transformants grown. The amplified phages are transferred onto a nylon membranes such as gene screening plus or a nitrocellulose filter and treated with an alkali to remove protein to obtain λphage DNA or plasmid DNA containing cDNA. The DNAs of cDNA clone are hybridized with $^{32}$P-labeled probe, which has been prepared from DNA fragments of previously cloned bovine chondromodulin gene in a conventional manner or using commercially available kit or the like, and selected by plaque hybridization according to the method described in Molecular Cloning, Cold Spring Harbor Laboratory, p. 320–328 (1982) to yield complete or a part of cDNA encoding hChM-I.

A partial fragment of human chondromodulin-I gene can be obtained by polymerase chain reaction (PCR) using PCR primers designed on the basis of amino acid sequence of bovine chondromodulin-I protein. As a template, cDNA synthesized on the basis of RNA extracted from human chondrosarcoma or human normal chondrocyte in a conventional manner can be used. A gene encoding the entire sequence of human chondromodulin-I protein can be obtained by carrying out PCR repeatedly, by carrying out PCR with primers designed on the basis of a primer(s) used in the synthesis of template cDNA, or by carrying out PCR with primers based on appropriate anchor sequence attached at the 3' end of said cDNA.

Alternatively, a synthetic oligonucleotide prepared on the basis of DNA sequence deduced from the amino acid sequence of chondromodulin-I protein is also available.

DNA can be prepared from positive plaques after the amplification of phages as described (T. Maniatis et al., Molecular Cloning, Cold Spring Harbor Laboratory, Cold Spring Harbor, N.Y., 85 (1982)), digested with an appropriate restriction enzyme such as EcoRI or the like, and subcloned into a plasmid such as pUC18, and the base sequence of desired cDNA segment can be determined by, for example, dideoxy method (Sanger et al., Proc. Natl. Acad. Sci. U.S.A., 74: 5463, (1977)). Thus obtained base sequence, for example, that shown in the SEQ ID NO: 2, 3, 4, 5, 6 or 7, is a fragment of 892 or 1006 nucleotides long in total and encodes a protein having 296 or 334 amino acids, wherein said protein contains the amino acid sequence of the mature protein. Base sequences shown in SEQ ID NO: 2, 3 and 4 contains partly a base sequence(s) of bovine gene though, the amino acid sequences coded by them are in agreement with that of human chondromodulin-I protein.

As previously mentioned, the present invention is inclusive of DNA derivatives obtained by conventional methods for the modification as far as said derivatives encodes the active chondromodulin-I protein of the invention.

As the DNA encoding chondromodulin-I protein was cloned and its sequence was determined in the present invention, one can easily construct expression vectors which enable host cells to produce chondromodulin-I protein using the known recombinant technology for example, by inserting into a known expression vector the DNA compound, after modification of 5' terminal at an appropriate site of the vector, downstream from a promoter, using a well known method per se, and introducing the expression vector harboring the cDNA into a host cell such as *Escherichia coli* cell, yeast cell, animal cell or the like according to the method known to one of skill.

This invention can be accomplished using any expression vectors having a promoter at an appropriate site to make the DNA encoding chondromodulin-I protein expressed in a selected host cell.

To accomplish the industrial production of human chondromodulin-I protein, it is necessary to construct a stable host-vector system which can express biologically active protein. Factors that must be considered are: naturally-occurring human chondromodulin-I protein is a glycosylated protein; human chondromodulin-I molecule contains a lot of cysteine residues whose refolding affect greatly on the acquisition of physiological activity; and the expression product must be processed in living body (cells) to mature-type human chondromodulin-I protein. Taking into account these factors, animal cells are preferred as hosts for purposes of the present invention.

Examples of host cells usable for transformation include animal cells described in working Examples below. However, it is not restrictive and other host cells such as microorganisms or insect cells or the like can be used.

Animal cells usable in the present invention are CHO cell, COS cell, mouse L cell, mouse C127 cell, mouse FM3A cell and the like. These cells have advantage that they can produce and secrete mature-type hChM-I by introducing a gene encoding hChM-I in the form of precursor protein.

When these cells are used as hosts, expression plasmids preferably contain SV40 promoter, metallothionein gene promoter or the like. An expression vectors can be constructed by inserting hChM-I gene modified to have signal sequence from 5' terminal downstream from a promoter. To achieve higher expression, i.e., to increase the yield of expression product, the expression vector may contain two or three hChM-I genes inserted in such a manner that. genes are connected tandemly from 5' to 3' direction. Alternatively, 2–3 genes each having a promoter such as SV40 promotor attached to its 5' site can be connected tandemly. A polyadenylation site, for example, one derived from SV40 DNA, β-globin gene or metallothionein gene is placed downstream from the hChM-I gene.

Expression vectors may contain a gene that serves as a marker for selection when transformed into animal cells such as CHO cell. Examples of selectable marker are DHFR gene that gives methotrexate-resistance and 3'-deoxycistoleptamine antibiotic G-418 gene and the like. In an expression vector, at 5' and 3' sites of the selected drug-resistant marker are inserted a promoter such as SV40 promoter and a polyadenylation site, respectively. It can be accomplished by inserting a marker gene into hChM-I expression vector downstream from polyadenylation site of hChM-I gene. Expression vectors may not contain selectable marker for transformants. In such a case, double-transformation will be carried out using hChM-I expression vector and a vector containing selectable marker in transformants such as pSV2neo, pSV2gpt, pMTVdhfr or the like.

Animal cells transformed by the double-transformation can be selected on the basis of phenotype as mentioned above due to the expression of selectable marker. After host cells in which hChM-I has been expressed are detected, double-transformation can be repeatedly conducted using different selectable marker so as to increase the yield of expression product hChM-I.

Example of plasmid vector useable as an expression/vector is pKCR (Proc. Natl. Acad. Sci. U.S.A., 78, 1528 (1981)) containing SV40 early promoter, splicing sequence DNA derived from rabbit β-globin gene, polyadenylation site derived from rabbit β-globin gene, polyadenylation site derived from SV40 early promoter, and origin of transcription and ampicillin-resistant gene derived from pBR322.

Generally, expression vector is introduced into animal cells by transfection with calcium phosphate. Cultivation of transfectants can be carried out in a conventional manner by means of suspension culture or adhesion culture in a medium such as MEM, RPMI1640 or the like in the presence of 5–10% serum or appropriate amount of insulin, dexamethasone, transferrin, or in a serum-free medium. Animal cells expressing hChM-I are expected to secrete hChM-I in culture supernatant and therefore it is possible to carry out separation and purification of hChM-I using the supernatant of cultured broth of transformants. The culture supernatant containing hChM-I can be purified by means of chromatography using heparin sepharose, blue sepharose or the like.

Expression vectors functional in microorganisms such as *Escherichia coli, Bacillus subtilis* or the like will preferably comprise promoter, ribosome binding (SD) sequence, chondromodulin-I protein-encoding gene, transcription termination factor, and a regulator gene.

Examples of promoters include those derived from *Escherichia coli* or phages such as tryptophane synthetase (trp), lactose operon (lac), λphage $P_L$ and $P_R$, $T_5$ early gene $P_{25}$, $P_{26}$ promoter and the like. These promoter may have modified or designed sequence for each expression vector such as pac promoter (Agr. Biol. Chem., 52: 983–988, 1988).

Although the SD sequence may be derived from *Escherichia coli* or phage, a sequence which has been designed to contain a consensus sequence consisting of more than 4 bases, which is complementary to the sequence at the 3' terminal region of 16S ribosome RNA, may also be used.

The transcription termination factor is not essential. However, it is preferable that an expression vector contains a ρ-independent factor such as lipoprotein terminator, trp operon terminator or the like.

Preferably, these sequences required for the expression of the chondromodulin-I protein gene are located, in an appropriate expression plasmid, in the order of promoter, SD sequence, chondromodulin-I protein gene and transcription termination factor from 5' to 3' direction.

It is known that the copy number of a transcription unit on a vector can be increased by inserting more than one unit composed of SD sequence and hChM-I gene (Japanese Patent Laid-open No. 95798/1989), which method can be applied to the present invention.

Typical examples of expression vector are pVAI2 (Japanese Patent Laid-open No. 95798/1989) and commercially available pKK233-2 (Pharmacia). However, a series of plasmids pGEK (Pharmacia), which are provided for the expression of fused proteins, are also employable for the expression of the chondromodulin-I protein gene of the present invention.

A suitable host cell can be transformed with an expression vector comprising the DNA encoding chondromodulin-I protein in a conventional manner to give a transformant.

The cultivation of the transformants can be carried out using any of the well known procedures in literatures such as Molecular Cloning (1982), and the like.

The cultivation is preferably conducted at a temperature from about 28° C. to 42° C.

Expression vectors used for transforming other host cells, such as those derived from insects or animals including mammals, consist of substantially the same elements as those described in the above. However, there are certain preferable factors as follows.

When insect cells are used, a commercially available kit, MAXBAC™ is employed according to the teaching of the supplier (MAXBAC™ BACULOVIRUS EXPRESSION SYSTEM MANUAL VERSION 1.4). In this case, it is desirable to make a modification to reduce the distance between the promoter of polyhedrin gene and the initiation codon so as to improve the expression of the gene.

Separation and purification of chondromodulin protein produced by transformants can be conducted using any one of known procedures to one of skill in the art.

The recombinant polypeptide expressed by the host cells such as microorganisms including *E. coli*, insect cells and animal cells can be recovered from the cultured broth by known methods and identified by, for example, immunoreactions between the expressed protein and a rabbit antiserum raised against a synthetic peptide containing a fragment of human chondromodulin-I protein, using a conventional method such as Western blot analysis.

Biological activities of chondromodulin protein can be determined according to the described method (Suzuki, et al., Methods in Enzymology, 146; 313–320, 1987).

Primary cells were isolated from growing costal cartilage obtained from a rabbit and grown in a 96-well plate. When the culture became confluent, [$^3$H]thymidine and 0.6 to 200 ng/ml of chondromodulin-I protein, and 0.4 ng/ml of FGF, if desired, were added to the plate and the uptake of [$^3$H]thymidine was determined. For control experiments, samples lacking chondromodulin-I protein and/or FGF were treated simultaneously.

The chondromodulin protein-I was also evaluated about the inhibiting activity against vascular infiltration by determining the preventive effect on the growth of vascular endothelial cells. The evaluation was based on the inhibition against [$^3$H]thymidine uptake by aortic endothelial cells as will be hereinafter described in detail in Examples. Thus, when chondromodulin protein was added to bovine aortic endothelial cells, the uptake of radioactive thymidine was apparently inhibited.

For application of hChM-I to clinical treatment, it is usable alone or as a pharmaceutical composition formulated with pharmaceutically acceptable carriers thesefor. The content of hChM-I, an active ingredient, can be 1–90% (w/w) related to carriers. For example, hChM-I of the present invention can be formulated as a medicine for external application and use in the treatment of fracture, cartilage disease or the like, which medicine can be prepared by, for example, mixing with, impregnating into, or applying onto physiologically acceptable carriers including collagen, aterocollagen, gelatin, hyaluronic acid, polyethylene glycol, polylactose, bone cement, hydroxyapatite, ceramics, carbon fiber, fibrin starch and the like. It can be orally administered after formulating into an appropriate form such as granules, fine granules, powders, tablets, hard capsules, soft capsules, syrups, emulsions, suspensions, solutions or the like. It can be formulated into injectable forms to be administered intravenously, intramuscularly, topically, or subcutaneously, or into suppositories. These formulations for oral, intrarectal or parenteral administration can be prepared using organic/inorganic carriers/diluents in the form of solid/liquid. Examples of excipient usable in solid formulations include lactose, sucrose, starch, talc, cellulose, dextrin, kaolin, calcium carbonate and the like. Liquid formulations for oral administration, for example, emulsions, syrups, suspensions and solutions, may contain inert diluents commonly used in the art such as water, plant oil or the like. Addition to the inert diluent, such a formulation can contain additives, for example, humectant, suspending aides, sweetening agents, aromatics, coloring agents, preservatives and the like. The liquid formulations may be included in capsules made of absorbable substance. Examples of solvent or suspending agent for parenteral formulations such as injections, suppositories or the like include water, propylene glycol, polyethylene glycol, benzyl alcohol, ethyl oleate, lecithin and the like. Example of bases for suppositories include cacao butter, emulsified cacao butter, laurin tallow, witepsol and the like. Preparation of these formulations can be carried out in a conventional manner.

The clinical dose of hChM-I of the present invention varies depending on the manner of administration, age, weight, and the condition of patient to be treated. Appropriate daily dosage of hChM-I of the present invention on oral or external administration to adult is generally about 1 ng–50 mg (for injection, 1/10 or less than 1/10 of this dosage), which may be administered once, in two to several divisions at appropriate intervals, or intermittently. For injection, it is preferable to administer the above-mentioned dose continuously or intermittently.

In case that hChM-I of the present invention is used with medicinal purposes, it may be in any form that can exert the biological and/or physiological activities of hChM-I, for example, purified hChM-I, recombinant hChM-I, cultured broth of transformants, separated transformants, treated transformants, immobilized transformants, crude enzyme solution, enzymatically-treated product and the like.

Following Examples further illustrate and detail the invention disclosed, but should not be construed to limit the invention.

EXAMPLE 1

Preparation of Probe DNA Fragment from Bovine Chondromodulin Gene

Plasmid DNA was obtained from cloned bovine chondromodulin gene (Hiraki et al., Biochemical and Biophysical Research Communications, 175, 971–977 (1991); and European Patent Publication No. 473,080) according to the method of T. Maniatis et al., Molecular Cloning, Cold Spring Harbor Laboratory, Cold Spring Harbor, N.Y., 85–96 (1982). Thus, a large amount of plasmid DNA containing bovine chondromodulin gene was recovered and purified from E. coli transformants harboring pUC19 vector containing at its EcoRI site an about 1.4 kb gene sequence of bovine chondromodulin gene encoding the whole protein.

The plasmid DNA (20 µg) was digested with restriction enzymes EcoRI (about 200 U) and PstI (about 200 U) at 37° C. for 2 hr and subjected to electrophoresis on agarose gel to separate vector DNA and bovine chondromodulin gene in a conventional manner. The gel was stained with ethydium bromide in a conventional manner and gel containing DNA fragment corresponding to bovine chondromodulin gene was cut out under UV light. The gel containing bovine chondromodulin gene was treated according to the method of Maniatis et al., Molecular Cloning, Cold Spring Harbor Laboratory, Cold Spring Harbor, 164–170 (1982) to recover and purify DNA fragment (about 2 µg) for probe. The DNA fragment (100 ng) was labeled with $^{32}$P using RTC DNA Labeling Kit (Pharmacia, Inc.) according to the manufacturer's instruction attached thereto.

EXAMPLE 2

Screening of Genomic DNA Clone Encoding a Part of Chondromodulin-I

Screening of human genomic library (Clonetech, Inc.) was conducted according to the instruction manual attached thereto. Approximately $10^6$ clones (about $2\times10^5$ clones/plate) of phage were transfected into E. coli strain P2-392 and grown in petri dishes (24.5×24.5 cm) each containing NZY soft-agar layered over 1.5% NZY agar plate at 37° C. overnight. The NZY medium was prepared by adding 0.25% magnesium sulfate to a solution (pH 7.5) of 1% NZ-amine, 0.5% yeast extract and 0.5% sodium chloride. The 1.5% NZY-agar plate was prepared by autoclaving NZY medium containing 1.5% agar powder. The NZY soft-agar was prepared by autoclaving NZY medium containing 0.7% agar powder. The plaque hybridization was carried out by transferring λphage clones in NZY soft-agar to nitrocellulose filter (BA85, S & S Inc.) by putting a filter on each plate and removing gently.

Thus, two nitrocellulose membranes were put on soft-agar in each plate and removed to transfer phages. The both membranes were marked equally to show the relative positions on the plate. Each membrane was placed for 2 min on a filter paper previously soaked with 0.2M sodium hydroxide/1.5M sodium chloride. After removal of fluid with dry filter paper, the membrane was placed on a filter paper previously soaked with 2×SSCP/0.2M Tris-HCl, pH 7.4 and air-dried on a dry filter paper. The same procedures were repeated. 2×SSCP: SSCP of twice of the concentration, the same expression will be used hereinafter; 10×SSCP= 1.2M sodium chloride, 150 mM sodium citrate, 130 mM potassium dihydrogen phosphate, 1 mM EDTA, pH 7.2.

The treated nitrocellulose membranes were heated at 80° C. for 2 hr to fix nucleic acid and washed twice with 3×SSC (20×SSC, i.e., SSC solution of 20 times of the concentration, consists of 3M sodium chloride, 0.3M sodium citrate)/0.1% SDS at 60° C. for 15 min. Each membrane was immersed in hybridization buffer [3×SSC, 0.1% SDS, 10×Denhardt's reagent (50×Denhardt=1% bovine serum albumin, 1% polyvinylpyrrolidone, 1% Ficol 400), 20 µg/ml denatured salmon sperm DNA and 10% dextran sulfate] (5 ml) and incubated at 65° C. for 3 hr.

Hybridization was performed by incubating the membranes in a hybridization buffer containing $^{32}$P-labeled DNA fragment previously prepared in Example 1 at a concentration of 5 ng/ml (converted to a template DNA basis) at 55° C. for 18 hr. The membranes were removed and washed in 3×SSC/0.1% SDS at room temperature for 30 min, which was repeated twice. The membranes were washed in 0.2× SSC/0.1% SDS at 55° C. for 15 min, which was repeated twice, dried and detected by autoradiography. Upon autography, there obtained one positive plaque which gave positive signal at corresponding positions on both of paired membranes. Clones corresponding to positive signal were recovered by punching the plaque on soft-agar with a glass tube and extracted with TMG buffer (50 mM Tris-HCl, pH 7.5, 100 mM sodium chloride, 10 mM magnesium chloride, 0.01% gelatin) (1 ml) in the presence of chloroform (50 µl) overnight. The extracted phage particles were subjected to plaque hybridization in a manner similar to that described above by transfecting into E. coli strain P2-392 in a conventional manner and culturing in 9 cm petri dishes in an appropriate amount. This series of procedures were repeated to purify the clone corresponding to the positive signal, resulting in an independent λ411 clone.

EXAMPLE 3

Subcloning of DNA Fragment Containing a Coding Region from Phage DNA and Sequence Analysis thereof DNA fragments were extracted from λ114 phage clones obtained in Example 2 and subcloned into plasmids pUC18 and pUC 19. A suspension of λphage clones ($2 \times 10^7$ p.f.u., plaque formation unit) in TMG buffer (200 µl) were infected into E. coli strain P2-392 ($2 \times 10^8$, 40 µl) in NZY medium (200 ml) in 500 ml Erlenmeyer flask at 37° C. for 15 min. After addition of 1M calcium chloride (1 ml), the flask was incubated overnight, i.e., about 14 hr. To the flask is added chloroform (2 ml) and it allowed to stand for 10 min. After sodium chloride (15.8 g) was dissolved, the mixture was centrifuged at 6,000 rpm at 4° C. for 20 min with Hitachi Cooling Centrifuge SCR20BB (Rotor RPR9-2). To the supernatant was dissolved poly(ethylene) glycol 6000 (20 g) and the solution allowed to stand for 1 hr on an ice-bath.

The mixture was centrifuged at 6,000 rpm for 20 min with Hitachi Cooling Centrifuge SCR20BB (Rotor RPR9-2) and the precipitates suspended in A buffer (0.5% NP40, 36 mM calcium chloride, 30 mM Tris-HCl, pH 7.5, 50 mM magnesium chloride, 125 mM potassium chloride, 0.5 mM EDTA, 0.25% DOC, 0.6 mM mercaptoethanol) (6 ml). Nucleic acids derived from E. coli were decomposed by incubating the suspension in the presence of 10 mg/ml deoxyribonuclease I (100 µl) and 10 mg/ml ribonuclease A (10 µl) at 30° C. for 30 min. To the reaction mixture is added an equal amount of chloroform and the mixture stirred thoroughly and centrifuged with Tomy Centrifuge LC-06 (Rotor-TS-7) at 3,000 rpm for 10 min to separate supernatant.

In centrifuge tube for Hitachi Ultracentrifuge Rotor RPS40T (Hitachi, Japan), 40% glycerol solution (0.5% NP40, 30 mM Tris-HCl, pH 7.5, 125 mM potassium chloride, 0.5 mM EDTA, 0.6 mM mercaptoethanol, 40% glycerol) (1 ml) was placed, which was layered with 10% glycerol solution (0.5% NP40, 30 mM Tris-HCl, pH 7.5, 125 mM potassium chloride, 0.5 mM EDTA, 0.6 mM mercaptoethanol, 10% glycerol) (3 ml). The nuclease-treated phage suspension prepared above was layered over these glycerol solutions and centrifuged with Hitachi Ultracentrifuge 70P72 (Rotor RPS40T; Hitachi, Japan) at 35,000 rpm for 1 hr. Precipitated phage particles were suspended in a mixture (0.4 ml) of 40 mM Tris-HCl, pH 7.5, 10 mM EDTA and 2% SDS and the suspension incubated at 55° C. for 1 hr in the presence of 10 mg/ml proteinase K (4 µl). The solution was transferred to Eppendorph tube and extracted with an equal volume of phenol/chloroform. The extract was subjected to ethanol precipitation to yield objective phage DNA (200 µg).

The resultant phage DNAs (10 µg) were digested with restriction enzymes BamHI and SalI (20 units each; Takara Syuzo, Japan) in a restriction buffer as specified in manual at 37° C. for 3 hr and the digestion mixture was electrophoresed on agarose gel in a conventional manner. Southern hybridization conducted using DNA probe prepared in Example 1 according to the method described in Molecular Cloning, Cold Spring Harbor Laboratory, Cold Spring Harbor, 382–389 (1982) revealed the presence of a DNA fragment at about 5.6 kb band, to which the probe hybridized most strongly.

The objective DNA fragment was separated and purified by digesting phage DNAs (100 µg) with restriction enzymes BamHI and SalI and recovering DNA fragment from agarose gel in a conventional manner. The DNA fragments (about 100 ng) were ligated into pUC18 and pUC19 plasmid vectors (200 ng) previously digested with restriction enzymes BamHI and SalI in a conventional manner in the presence of T4 DNA ligase (350 units) in a reaction buffer (66 nm tris-HCl (pH 7.6), 6.6 mM magnesium chloride, 10 mM dithiothreitol, 66 µM ATP, substrate DNA) (10 µl). The ligation mixture (1 µl) was used to transform competent E. coli DH5α (COMPETENT HIGH, Toyobo, Japan) and the resultant bacterial solution was spread onto LB agar medium (1% yeast extract, 0.5% bacto-trypton, 0.5% sodium chloride) containing ampicillin (50 µg/ml) in 15 cm petri dish. Ampicillin-resistant colonies appeared on dish (5 ml each) were grown. Plasmid DNAs were recovered according to the method of Maniatis et al., Molecular Cloning, Cold Spring Harbor Laboratory, p. 365–370 (1982), digested with restriction enzymes BamHI and SalI and analyzed on agarose gel electrophoresis. The analysis revealed that a recombinant named p411BS containing the objective 5.6 kb DNA fragment was obtained.

Plasmid DNA was prepared from one of positive clones in a conventional manner (Molecular Cloning, Cold Spring Harbor Laboratory, p. 86–96 (1982)) and DNA regions necessary for sequencing were digested with a restriction enzyme(s) into fragments, which were subcloned into plasmid vector pUC19. From the resultant subclones were prepared plasmid DNAs in a conventional manner and subjected to sequence analysis. Both (+)- and (−)-strands of the DNA fragment were determined using as sequence primers two synthetic primers shown below and in SEQ ID NO: 9 and 10, respectively.

SEQ ID NO: 9: 5'-d(GTAAAACGACGGCCAGT) 3'

SEQ ID NO: 10: 5'-d(CAGGAAACAGCTATGAC) 3'

Result is shown in SEQ ID NO: 1. The analysis revealed that the plasmid p411BS derived from independent λ411 clone contains 5' upstream sequence, that is, a part of coding region (exon) corresponding to N-terminal region (amino acid No. 1-72) of hChM-I as well as intron sequence(s).

EXAMPLE 4

Preparation of cDNA

The synthesis of cDNA was carried out using a primer prepared by heating a mixture of 1.2 µg/µl of a synthetic DNA (e.g., a DNA of SEQ ID NO: 11) containing NotI and, at its 5' end, XhoI restriction sites, and 40 Ts at the 3' end of NotI restriction site of one strand, which is shown by the following sequence:

5'-d(CTCGAGGCCATGGCGGCCGCTTTTTTTTTTTTTTTTTTTTTTTTTTTTTT

TTTTTTT) 3' and 0.4 µg/µl of a complementary DNA (e.g., a DNA of SEQ ID NO: 12) lacking the cluster of T of the following sequence:

5'-d(GCGGCCGCCATGGCCTCGAG) 3' at 95° C. for 5 min and incubating at 36° C. for 1 hr for annealing.

RNA was prepared as follows. Human chondrosarcoma tissue (10 g) is pulverized in liquid nitrogen, homogenize in aqueous guanidium isothiocyatate solution, and subjected to cesium chloride equilibrium density gradient centrifugation according to the method of Chirgwin et al., Biochemistry, 18, 5294–5299 (1979) to obtain total RNA (about 1 mg). The total RNA is then purified using oligo(dT)cellulose type 7 (Pharmacia) according to a conventional method (Molecular Cloning, Cold Spring Harbor Laboratory, Cold Spring Harbor, N.Y., 85 (1982)) to obtain polyA$^+$ RNA).

The polyA$^+$ RNA (about 1 µg) was reacted with the primer (80 pmole) previously prepared by annealing in a reaction buffer [50 mM Tris-HCl (pH 8.3), 50 mM potassium chloride, 8 mM magnesium chloride, 1 mM 4dNTPs (dATP, dGTP, dCTP, dTTP), 10 mM DTT (dithiothreitol) and 40 µCi $\alpha$-$^{32}$P-dCTP] (50 µl) in the presence of AMV reverse transcriptase (100 units) at 37° C. to obtain the first strand cDNA hybridized with template RNA.

EXAMPLE 5

PCR and Analysis of DNA Fragment Amplified Thereby

PCR was carried out with Perkin Elmer Cetus DNA Thermal Cycler using Gene Amp DNA Amplification Reagent Kit (Takara Syuzo, Japan) according to the manufacturer's instructions. As a template DNA, a reaction mixture (1 µl) of cDNA synthesis described in Example 4 was used. To the template solution is added ×10 reaction buffer (500 mM KCl, 100 mM Tris-HCl (pH 8.3), 15 mM MgCl$_2$, 0.1% (w/v) gelatin) (10 µl), 1.25 mM 4dNTPs (16 µl), 20 µM primer #1 and #2 (5 µl each), Taq DNA polymerase (0.5 µl) to yield a reaction system (100 µl). PCR was conducted by repeating 35 times of reaction cycle comprising the following steps: pre-treatment at 94° C. for 10 min, denaturation at 94° C. for 1 min, annealing at 44° C. for 1.5 min and elongation at 72° C. for 2 min. The reaction was stopped by incubating at 72° C. for 7 min.

Primers #1 and #2 are DNA primers of 19 and 16 nucleotides each being shown in SEQ ID NO: 13 and 14, respectively, having the following sequences.

Primer #1: 5'-d(AGTCTCCAAGTGCCTCACT) 3'

Primer #2: 5'-d(CGAGGCCATGGCGGCC) 3'.

The primer #1 is the upstream sequence of a gene designed on the basis of the human gene obtained in Example 3, while the primer #2 is a DNA fragment complementary to a part of the sequence shown in SEQ ID NO: 12 which has been used as a primer in the synthesis of cDNA.

The second PCR was carried out using a portion (2 µl) of the reaction solution obtained above as substrate and primers #3 and #4, which are DNA primers of 18 nucleotides shown in SEQ ID NO: 15 and 16, respectively, and have the following sequence.

Primer #3: 5'-d(CATGACAGAGAACTCCGA) 3'

Primer #4: 5'-d(ACACCATGCCCAGGATGC) 3'

The primer #3 is a sequence corresponding to the beginning part of the region encoding hChM-I designed on the basis of the human gene obtained in Example 3, while the primer #4 is a sequence corresponding to the end part of a sequence encoding bovine chondromodulin-I protein. The 2nd PCR was carried in a manner similar to that used in the 1st PCR, that is, using the same reaction buffer, dNTPs, enzyme treatment, in a reaction mixture adjusted to 100 µl with distilled water by repeating 35 times of reaction cycle comprising the following steps: pretreatment at 94° C. for 10 min, denaturation at 94° C. for 1 min, annealing at 55° C. for 1.5 min and elongation at 72° C. for 2 min. The reaction was stopped by incubating at 72° C. for 7 min.

The reaction mixture (10 µl from 100 µl) was analyzed by agarose gel electrophoresis and gel corresponding to about 1 kb band was cut out to recover DNA fragment in a conventional manner. DNA recovered from the gel was extracted with phenol/chloroform (1:1), precipitated with ethanol and dissolved in sterilized deionized water (20 µl). DNA is ligated into a cloning site of a commercially available pCR2 vector (Invitrogen, Inc.) by reacting the DNA solution (5 µl) obtained above with pCR2 vector (0.25 µg) in the presence of T4 DNA ligase (300 units) in a reaction buffer (66 mM tris-HCl (pH 7.6), 6.6 mM magnesium chloride, 10 mM dithiothreitol, 66 µM ATP, substrate DNA) at 16° C. for 12 hr.

The ligation mixture (3 µl) was use to transform competent E. coli JM109 (COMPETENT HIGH, Toyobo, Japan) and the resultant bacterial solution was spread onto X-Gal-IPTG-LB agar medium (1% yeast extract, 0.5% bactotrypton, 0.5% sodium chloride, 0.004% X-Gal, 1 mM IPTG) containing ampicillin (50 µg/ml) in 15 cm petri dish. Twelve colonies which are ampicillin resistant and do not show color development due to X-Gal were selected from colonies on the petri dish, and each (5 ml) was grown. Plasmid DNA was then recovered according to the method of Maniatis et al., Molecular Cloning, Cold Spring Harbor Laboratory, p. 365–379 (1982), digested with restriction enzyme EcoRI and analyzed by means of electrophoresis on agarose gel. The analysis revealed that there obtained three transformants each containing plasmid DNA phCHM-13-6, phCHM-16-3 or phCHM16-5, which plasmid gives DNA fragment of different size upon EcoRI digestion.

Plasmid DNAs were prepared from each of purified positive clones, phCHM-13-6, phCHM-16-3 and phCHM16-5, in a conventional manner (Molecular Cloning, Cold Spring Harbor Laboratory, p. 86–96 (1982)) and sequenced with Fluorescence Sequencer GENESIS 2.000 System. Both of (+)- and (−)-strand of the DNA were determined using as sequence primers two different synthetic primers shown in SEQ ID NO: 9 and 10, respectively.

SEQ ID NO: 9: 5'-d(GTAAAACGACGGCCAGT) 3'

SEQ ID NO: 10: 5'-d(CAGGAAACAGCTATGAC) 3'

On the basis of the sequence obtained above, synthetic DNAs complementary to several partial sequences were prepared and subjected to sequencing in a similar manner to obtain base sequences shown in SEQ ID NO: 2, 3 and 4 together with corresponding amino acid sequences deduced therefrom.

EXAMPLE 6

Cloning of 3'-Downstream Sequence of Gene Encoding Chondromodulin

The sequence of 3'-downstream coding region of clones phCHM-13-6, phCHM-16-3 and phCHM16-5 obtained in Example 5 above corresponded to the DNA primer (5'-d (ACACCATGCCCAGGATGC) 3'; SEQ ID NO: 16), which is 18 nucleotides synthetic DNA based on bovine chondromodulin gene and was used in the 2nd PCR. To obtain the region corresponding to said DNA primer of SEQ ID NO: 16 and also a region downstream therefrom which has human base sequence, cloning was carried out again by PCR.

RNA was prepared as follows. Human normal costochondral tissue (about 20 g) was pulverized in liquid nitrogen, homogenized in aqueous guanidium isothiocyatate solution, and subjected to cesium chloride equilibrium density gradient centrifugation according to the method of Chirgwin et al., Biochemistry, 18, 5294–5299 (1978) to obtain total RNA (about 2 mg).

The total RNA (20 μg) was then reacted with a primer (80 pmole) previously annealed in a manner similar to that used in Example 4 in reaction buffer [50 mM Tris-HCl (pH 8.3), 50 mM potassium chloride, 8 mM magnesium chloride, 1 mM 4dNTPs (dATP, dGTP, dCTP, dTTP), 10 mM dithiothreitol and 40 μCi α-$^{32}$P-dCTP] (50 μl) in the presence of AMV reverse transcriptase (100 units) at 37° C. to obtain the first strand cDNA hybridized with template RNA. A portion of the resulting reaction solution was used as template in the PCR.

PCR was carried out with Perkin Elmer Cetus DNA Thermal Cycler using Gene Amp DNA Amplification Reagent Kit (Takara Syuzo, Japan) according to the manufacturer's instruction using, as template, a portion (1 μl) of the reaction solution obtained in the cDNA synthesis using total RNA as described above. To the solution are added ×10 reaction buffer (500 Mm KCl, 100 mM Tris-HCl (pH 8.3), 15 mM MgCl$_2$, 0.1% (w/v) gelatin) (10 μl), 1.25 mM 4dNTPs (16 μl), 20 μM primers #5 and #2 (5 μl each) and Taq DNA polymerase (0.5 μl) to yield a reaction system (100 μl). PCR was conducted by repeating 35 times of reaction cycle comprising the following steps: pre-treatment at 94° C. for 10 min, denaturation at 94° C. for 1 min, annealing at 55° C. for 1.5 min and elongation at 72° C. for 2 min. Finally, the reaction was stopped by incubating at 72° C. for 7 min.

Primers #5 and #2 are DNA primers of 16 nucleotides each being shown in SEQ ID NO: 17 and 14, respectively, having the following sequence:

SEQ ID NO: 17: 5'-d(CCCTAGACTGGATCAC) 3'

SEQ ID NO: 14: 5'-d(CGAGGCCATGGCGGCC) 3'.

The primer #5 is the sequence of coding region of a gene designed on the basis of the human gene obtained in Example 5, while the primer #2 is a DNA fragment complementary to a part of the sequence shown in SEQ ID NO: 12 which has been used as a primer in the synthesis of cDNA.

The reaction mixture (10 μl from 100 μl) was analyzed by agarose gel electrophoresis and a gel corresponding to about 0.6 kb band was cut out in a conventional manner to recover DNA fragment. The DNA fragment was extracted with phenol/chloroform (1:1), precipitated with ethanol and dissolved in sterilized deionized water (20 μl). The DNA was ligated into a cloning site of commercially available pCR2 vector (Invitrogene) by reacting the DNA solution (5 μl) obtained above with pCR2 vector (0.25 μg) (Invitrogen, Inc.) in the presence of T4 DNA ligase (350 units) in a reaction buffer (66 mM tris-HCl (pH 7.6), 6.6 mM magnesium chloride, 10 mM dithiothreitol, 66 μM ATP, substrate DNA) at 16° C. for 12 hr.

The ligation mixture (3 μl) was used to transform competent E. coli JM109 (COMPETENT HIGH, Toyobo, Japan) and the resultant bacterial solution was spread onto X-Gal-IPTG-LB agar medium (1% yeast extract, 0.5% bactotrypton, 0.5% sodium chloride, 0.004% X-Gal, 1 mM IPTG) containing ampicillin (50 μg/ml) in 15 cm petri dish. Twelve colonies which are ampicillin resistant and do not show color development due to X-Gal were selected from colonies appeared on the petri dish, and each (5 ml) was grown. Plasmid DNA was then recovered according to the method of Maniatis et al., Molecular Cloning, Cold Spring Harbor Laboratory, p. 365–370 (1982), digested with restriction enzyme EcoRI and analyzed by electrophoresis on agarose gel. The analysis revealed that there obtained two transformants, phCHM-ILAST8 and phCHM-ILAST12, which give about 0.6 kb DNA fragments other than vector DNA fragments upon digestion with restriction enzyme EcoRI. 16-3 or phCHM16-5, which give DNA fragment of different size upon EcoRI digestion.

Plasmid DNAs were prepared from both purified clones phCHM-ILAST8 and phCHM-ILAST12 in a conventional manner (Molecular Cloning, Cold Spring Harbor Laboratory, p. 86–96 (1982)) and sequenced with Fluorescence Sequencer GENESIS 2,000 System (Dupont). Both of (+)- and (−)-strand of the DNA were determined using as sequence primers two different synthetic primers shown in SEQ ID NO: 9 and 10, respectively.

SEQ ID NO: 9: 5'-d(GTAAAACGACGGCCAGT) 3'

SEQ ID NO: 10: 5'-d(CAGGAAACAGCTATGAC) 3'

On the basis of the sequence obtained above, synthetic DNAs complementary to several partial sequences were prepared and subjected to sequence analysis in a similar manner, which showed that sequences of phCHM-ILAST8 and phCHM-ILAST12 are in agreement. As a result, the 3'-downstream sequence comprising a base sequence of SEQ ID NO: 8 was obtained.

EXAMPLE 7

Construction of Expressing Plasmid Encoding Human Chondromodulin-I Protein

Comparison of base sequences of clones phCHM-ILAST8 and phCHM-ILAST12 obtained in Example 6 and those of phCHM-13-6, phCHM-16-3 and phCHM16-5 obtained in Example 5 revealed that the former two varied from the latter in 2 bases in a sequence corresponding to 3'-downstream coding region, that is, the sequence corresponding to DNA primer (5'-d (ACACCATGCCCAGGATGC) 3') (18 nucleotides shown in SEQ ID NO: 16) used in the 2nd PCR. The former 2 clones, however, do not have variation in amino acid sequences compared to the latter. This means that clones phCHM-13-6, phCHM-16-3 and phCHM16-5 obtained in Example 5, when transformed into host cells, can allow the resultant transformants express perfect hChM-I regarding amino acid sequence, even if they are coded by a base sequence comprising, in part, that of bovine chondromodulin gene.

Plasmid DNA was obtained from cDNA clones phCHM-13-6, phCHM-16-3 or phCHM16-5 prepared in Example 5 according to the method of Maniatis et al., Molecular Cloning, Cold Spring Harbor Laboratory, p. 86–96 (1982). Each of plasmid DNAs phCHM-13-6, phCHM-16-3 and phCHM16-5 was digested with restriction enzymes NotI and NsiI to obtain about 1 kb DNA fragment containing part of vector sequence from respective clones. These DNA fragments covered the whole region encoding hChM-I, that is, the region extending from the translation initiation codon ATG through the stop codon TAA. Each of the DNA fragments recovered from cDNA clones phCHM-13-6, phCHM-16-3 and phCHM16-5 was ligated into commercially available expression vector pcDNAIneo (Invitrogen, Inc.) previously digested with restriction enzymes NotI and NsiI in reaction system (10 μl) containing T4 DNA ligase in a conventional manner. The ligation mixture was used to transform competent $E.\ coli$ DH5α (COMPETENT HIGH, Toyobo, Japan) and the resultant bacterial solution was spread onto LB agar medium (1% yeast extract, 0.5% bacto-trypton, 0.5% sodium chloride) containing ampicillin (50 μg/ml) in 15 cm petri dish. Ampicillin-resistant colonies (5 ml each) were grown. Plasmid DNAs were recovered according to the method of Maniatis et al., Molecular Cloning, Cold Spring Harbor Laboratory, p. 365–370 (1982), digested with restriction enzymes NotI and NsiI and analyzed on agarose gel electrophoresis. The analysis revealed that desired recombinants transformed with plasmid DNAs pcDNAhCHM-13-6, pcDNAhChM-16-3 and pcDNAhChM16-5 each containing, at the restriction sites NotI and NsiI of expression vector pcDNAIneo, each of objective hChM-I cDNA fragment were obtained.

From recombinant $E.\ coli$ cells were recovered and purified plasmid DNAs according to the method of Maniatis et al., Molecular Cloning, Cold Spring Harbor Laboratory, p. 86–96, (1982) to obtain a large amount of hChM-I expression plasmid DNAs.

EXAMPLE 8

Expression of hChM-I in Animal Cells

COS cells were transfected with either of expression plasmids pcDNAhCHM-13-6, pcDNAhChM-16-3 and pcDNAhChM16-5 constructed in Example 6 by the use of commercially available lipofectin reagent (LIPOFECTIN™, GIBCO, Inc.) according to the manufacturer's instruction.

Thus, COS cells were grown in DMEM medium in 9 cm petri dish. After removal of medium, cells were washed twice with PBS(–) solution (0.8% sodium chloride, 0.02% potassium chloride, 0.144% disodium hydrogen phosphate, 0.024% sodium dihydrogen phosphate, pH 7.4). After removal of PBS(–) solution, serum-free DMEM medium (8 ml) was added to the plate. A DNA solution to be used in transfection has been prepared by dissolving plasmid pcDNAhCHM-13-6, pCDNAhChM-16-3 or pcDNAhChM16-5 DNA (20 μg) in serum-free DMEM medium (100 μl) in No. 55,426,013 tube (Amersham, Inc.). To the DNA solution is added a mixture of lipofectin reagent (LIPOFECTIN™, GIBCO, Inc.) (50 μl) and serum-free DMEM medium (50 μl) and allowed to stand for 15 min at room temperature. The lipofectin-DNA suspension (200 μl) was added to COS cells washed with PBS(–) prepared above and cells grown at 37° C. for overnight under an atmosphere of 5% $CO_2$. After removal of lipofectin-containing medium, 10% FCS-containing ERDF medium (Kyokutoseiyaku, Inc.) was added to 10 cm petri dish and incubation continued at 37° C. for about 56 hr under an atmosphere of 5% $CO_2$.

Cultured broth was collected and the presence of physiological activity of hChM-I was confirmed according to a known method (Suzuki, et al., Methods in Enzymology, 146: 313–320 (1987)). The expression of hChM-I was confirmed by Western blotting conventionally.

EXAMPLE 9

Evaluation of Activities of Human Chondromodulin Protein

Isolation and cultivation of cells used in the experiments and the evaluation of activities were carried out substantially in accordance with the described method (Suzuki, et al., Methods in Enzymology, 146: 313–320, 1987). Cells were isolated from growing costal cartilage excised from a young New Zealand strain rabbit (400–600 g in weight) and suspended into a 1:1 mixture (hereinafter, referred to as FAD medium) of Ham's F-12 medium and Dulbecco's modified medium containing 10% fetal bovine serum (FCS) at a cell density of $10^5$ cells/ml. The cell suspension (0.1 ml) was dispersed into 96-well plate, which had been coated with type I collagen (50 μg/ml) overnight and washed with FAD medium, and incubated at 37° C. under atmosphere of 5% $CO_2$ with changing the medium every other day.

The DNA-synthetic activity was evaluated as follows. Cells were grown in the above 96-well plate until the culture became confluent, then the cells were grown in FAD medium containing 0.3% FCS for 24 hr. The culture was incubated for 22 hr in 0.1 ml of FAD medium containing 0.06 to 20 ng of cultured broth of transformants containing hChM-I, 0.04 ng of FGF (fibroblast growth factor) and 0.3% FCS. The cultivation was continued another 4 hr after the addition of 10 μl of [$^3$H]thymidine (130 μCi/ml) and cells were washed three times with ice-cold phosphate-buffered saline (20 mM phosphate buffer, pH7.0, 0.15M sodium chloride), extracted with 5% trichloroacetic acid and then with ethanol/ether (3:1 in volume). After the extraction, the precipitate left was dissolved in 0.3M sodium hydroxide, neutralized with 1/20 volume of 6N HCl and the radioactivity was detected by means of a scintillation counter. The uptake of radioactive thymidine observed when hChM-I and FGF were used simultaneously was higher than that observed when FGF used alone, demonstrating that the hChM-I possesses a potent stimulating effect on the growth of chondrocyte.

The inhibition activity of chondromodulin protein against the growth of vascular endothelial cells was evaluated using bovine aortic endotheliocytes. Thus, bovine aortic endotheliocytes were inoculated into α-MEM medium containing 0.1 ml of 20% FCS in a 96-well plate at a cell density of $2\times10^3$ cells/well and grown in a $CO_2$ incubator at 37° C. for 48 hr, when the medium was replaced by a freshly prepared one and 0 to 3 μg/ml of cultured broth of transformants containing hChM-I added thereto. After 12-hour incubation at 37° C., [$^3$H]thymidine was added to each well (1 μCi/well) and the plate was allowed to stand for 4 hr at 37° C. After the completion of the uptake of radioactively-labeled thymidine, cells were harvested using cell harvester and radioactivity detected on LKB plate. The uptake of radioactive thymidine was prevented when hChM-I was added, indicating that hChM-I possesses an activity to prevent the endothelial cells from growing.

As is clear from description above, hChM-I of the present invention is novel protein originated from human. By the use of gene encoding hChM-I, one can provide sufficient amount of recombinant hChM-I constantly and steadily. The hChM-I has activities to stimulate the growth of chondrocyte, to promote the differential potency of chondrocyte and to inhibit the growth of endothelial cells, and can be useful as an active ingredient of medicinal drugs. The hChM-I of the present invention is distinct from conventional bovine chondromodulin protein in amino acid sequence, base sequence of gene encoding the same and the like, and is considered to be less antigenic and more effective when used in treatment of human.

We claim:

1. An isolated human chondromodulin-I protein, which is a water-soluble protein composed of one polypeptide, which has a molecular weight of about 26,000 dalton on SDS-polyacrylamide gel electrophoresis; which has an ability to stimulate the growth of chondrocytes in the presence or absence of fibroblast growth factor and to inhibit the growth of vascular endothelial cells; and which is prepared by culturing a host cell which is transformed with an expression vector comprising DNA with encodes the amino acid sequence shown in SEQ ID NO: 19, 20 or 21 in culture medium to express a precursor protein of said human chondromodulin-I protein having said amino acid sequence, wherein said precursor protein is processed by said host cell to form said human chondromodulin-I protein, and recovering said protein from the resultant culture medium.

2. A pharmaceutical composition comprising a therapeutically effective amount of the chondromodulin-I protein of claim 1 together with a pharmaceutically acceptable carrier, excipient or solvent therefor.

3. The isolated human chondromulin-I protein of claim 1, wherein the DNA comprises the nucleotide sequence shown in SEQ ID NO: 2, 3, 4, 5, 6 or 7.

4. The isolated human chondromodulin-I protein of claim 1, wherein the expression vector is plasmid pcDNAChM-13-6, pcDNAChM-16-3 or pcDNAChM16-5.

5. A method of stimulating the growth of chondrocytes in a human, which comprises administering to a human in need of such treatment an effective amount of the chondromodulin-I protein of claim 1.

6. A method of inhibiting the growth of endothelial cells in a human, which comprises administering to a human in need of such treatment an effective amount of the chondromodulin-I protein of claim 1.

7. An isolated chondromodulin-I protein containing the amino acid sequence shown in SEQ ID NO: 19, 20 or 21.

8. A composition comprising a chondromodulin-I protein comprising the amino acid sequence of SEQ ID No. 19, 20 or 21 together with a pharmaceutically acceptable carrier, excipient or solvent therefor.

* * * * *